United States Patent [19]

Tsushima et al.

[11] 4,323,676
[45] Apr. 6, 1982

[54] PROCESS FOR PREPARING CEPHALOSPORINS

[75] Inventors: Susumu Tsushima, Suita; Michiyuki Sendai, Osaka; Mitsuru Shiraishi, Suita, all of Japan

[73] Assignee: Takeda Chemical Industries, Ltd., Osaka, Japan

[21] Appl. No.: 182,616

[22] Filed: Aug. 29, 1980

Related U.S. Application Data

[60] Division of Ser. No. 46,708, Jun. 8, 1979, Pat. No. 4,245,088, which is a continuation of Ser. No. 882,914, Mar. 2, 1978, abandoned, which is a continuation of Ser. No. 660,408, Feb. 23, 1976, abandoned.

[30] Foreign Application Priority Data

Feb. 24, 1975 [JP] Japan .................................. 50-23158
Mar. 21, 1975 [JP] Japan .................................. 50-34714
Mar. 20, 1975 [JP] Japan .................................. 50-33759
Jan. 1, 1976 [JP] Japan .................................. 51-1274

[51] Int. Cl.$^3$ .......................................... C07D 501/20
[52] U.S. Cl. ................................. 544/22; 424/246; 544/16; 544/27; 544/30
[58] Field of Search .................. 544/16, 30, 22, 21, 544/26, 27; 424/246

[56] References Cited

U.S. PATENT DOCUMENTS

| | | | |
|---|---|---|---|
| 3,278,531 | 10/1966 | Cox et al. | 260/243 |
| 3,929,780 | 12/1975 | Weir | 544/16 |
| 4,094,978 | 6/1978 | Beeby | 544/16 |
| 4,112,087 | 9/1978 | Beeby | 544/16 |
| 4,245,088 | 6/1979 | Tsushima et al. | 544/16 |

OTHER PUBLICATIONS

Cephalosporins and Penicillins, 1972, pp. 151–166.
JCS, 1965, pp. 5015–5031 and 7020–7028.

*Primary Examiner*—Nicholas S. Rizzo
*Attorney, Agent, or Firm*—Wenderoth, Lind & Ponack

[57] ABSTRACT

Novel 3-acyloxymethyl-cephem compounds of the formula:

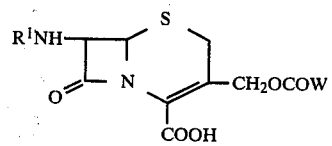

wherein $R^1$ is hydrogen or an acyl group; W is acetonyl, or a group represented by —X—COOH or —X—OH (X is an organic residue) or salts thereof were found to be useful as starting materials for preparing cephalosporins of the formula:

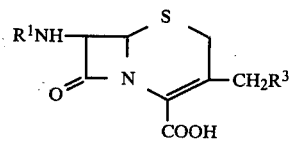

wherein $R^3$ stands for a residue nucleophilic compound and $R^1$ has the same meaning as above.

29 Claims, No Drawings

PROCESS FOR PREPARING CEPHALOSPORINS

This is a division of application Ser. No. 46,708, filed June 8, 1979, now U.S. Pat. No. 4,245,088, which is a continuation of application Ser. No. 882,914, filed Mar. 2, 1978, now abandoned, which in turn is a continuation of application Ser. No. 660,408, filed Feb. 23, 1976, now abandoned.

The present invention relates to novel 3-acyloxymethyl-cephem compounds and preparations thereof. More particularly, this invention relates to the compounds of the formula:

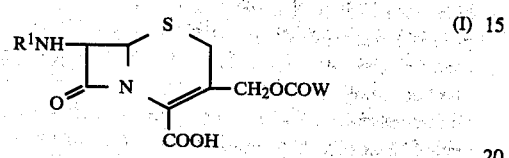

wherein $R^1$ is hydrogen or an acyl group; W is acetonyl or a group represented by —X—COOH or —X—OH (X is an organic residue) or salts thereof, for example pharmaceutically acceptable salts thereof, and also relates to processes for producing them.

Cephalosporin derivatives with a 3-hydroxymethyl moiety were only obtainable by enzymatic cleavage of the 3-acetyl group from 3-acetoxymethyl-cephalosporins or by separating them from the cephalosporin C fermentation byproduct. Recently, it has become possible to produce 7-(D-5-amino-5-carboxyvaleramido)-3-hydroxymethyl-3-cephem-4-carboxylic acid (desacetylcephalosporin C, DCPC) in high titer by fermentation (U.S. Pat. No. 3,926,726, Nature New Biology, 246, 154(1963)) and, alongside of cephalosporin C, this substance has been attracting attention as a starting material for cephalosporin compounds that could be more potent in antibiotic activity.

It has, however, been believed to be difficult to acylate the 3-hydroxymethyl group of the 3-hydroxymethyl compound (cephalosporadesic acid). For example, Heyningen [Van Heyningen: J.Med.Chem., 8, 22(1965), Advan. Drug. Res., 4, 28(1968)] reported that the O-acylation of cephalosporadesic acid was feasible only with the use of a large excess of aroyl chloride (yield 32%–57%) and that the use of ketene, aliphatic acid chloride or acetic anhydride did not cause the O-acylation, or induced a lactonization. Kukolja [J. Med.Chem. 13, 1114(1970)] reported a roundabout process for the synthesis of O-acyloxymethylcephalosporins which comprised O-acylating a 3-hydroxymethyl-2-cephem compound and then causing the latter to isomerize to the 3-cephem compound. U.S. Pat. No. 3,532,694 and Japanese Patent Publication No. 33080/1975 disclosed a process in which, to prevent the lactonization reaction, the 4-carboxyl group of cephalosporadesic acid is first protected, for example by esterification and, then, the O-acylation is carried out. Disclosed in Japanese Patent Application Laid Open No. 42792/1972 is a process which comprises O-acylating cephalosporadesic acid with azolide. However, these processes are not commercially profitable because they provide only low yields or/and involve troublesome and time-consuming procedures or/and expensive reagents, for instance. Thus, for example, the esterification reaction of cephalosporadesic acid cannot be accomplished by an ordinary esterification process in which the rearrangement of the double bond or the lactonization predominates. While it is possible to introduce such limited groups as methyl, ethyl, diphenylmethyl, benzyl, etc. by means of diazo compounds such as diazomethane, diazoethane, diphenyldiazomethane, phenyldiazomethane, etc., it is difficult, after 3-acylation, to de-esterify the compound without accompaniment of some side reaction such as a fission of the β-lactam ring or a shift of the double bond.

On the other hand, the reaction by which the 3-acetoxymethyl group of a cephalosporin compound is substituted with a nucleophilic reagent entails a concurrent decomposition of the starting material, intermediate and product in its course and a protracted reaction time, and therefore results in lower yields [A. B. Taylor, J. Chem. Soc., 7020(1965)]. Thus, it has been desired to have available a derivative possessing a group which will lend itself more readily to substitution than the acetoxy group.

To overcome the foregoing problems we undertook an extensive research, which led us to the finding that the use of diketene or compounds [III] [IV] hereinafter described as an acylating agent would enable cephalosporadesic acid to be O-acylated in high yield and that the O-acylated cephalosporin thus synthesized would undergo the desired substitution with a nucleophilic compound with great ease. This invention has been developed on the basis of the above findings.

The above compounds [I] include the compounds wherein $R^1$ is hydrogen, phenylacetyl, phenoxyacetyl, 5-amino-5-carboxyvaleryl whose amino or/and carboxyl groups may optionally be protected, or any of the groups found in the 6- or 7-positions of penicillin or cephalosporin derivatives as the case may be. Thus, for example, the acyl group $R^1$ may be selected from among aliphatic acyl groups such as formyl, acetyl, propionyl, butyryl, isobutyryl, valeryl, isovaleryl, cyclopentylcarbonyl, cyclohexylcarbonyl, cycloheptylcarbonyl, cyclopentylacetyl, cyclohexadienylacetyl, etc.; aromatic acyl groups such as benzoyl, p-nitrobenzoyl, toluoyl, naphthoyl, etc.; mono-substituted aliphatic acyl groups such as 2-thienylacetyl, cyanoacetyl, acetoacetyl, 4-chloro-3-oxobutyryl, 4-bromo-3-oxobutyryl, chloroacetyl, bromoacetyl, 4-methylthio-3-oxobutyryl, 4-carbamoylmethylthio-3-oxobutyryl, α-phenoxypropionyl, α-phenoxybutyryl, tetrazolylthioacetyl, tetrazolylacetyl, p-nitrophenylacetyl, trifluoromethylthioacetyl, trifluoromethylsulfinylacetyl, trifluoromethylsulfonylacetyl, cyanomethylthioacetyl, thiadiazolylthioacetyl, p-nitrophenylacetyl, (2-pyridyloxy)acetyl, (2-oxo-4-thiazolin-4-yl)acetyl, (2-imino-4-thiazolin-4-yl)acetyl, (2-thioxo-4-thiazolin-4-yl)acetyl, 4-pyridylthioacetyl, (3-sydnone)acetyl, 1-pyrazolylacetyl, 2-furylacetyl, (2-oxo-3-methylpyridazinyl)thioacetyl, (2-aminomethylphenyl)acetyl, (2-aminomethylcyclohexenyl)acetyl, etc., di-substituted aliphatic acyl groups such as α-carboxyphenylacetyl, mandelyl, α-sulfophenylacetyl, α-sulfo-(p-aminophenyl)acetyl, phenylglycyl, (4-hydroxyphenyl)glycyl, (4-methylthiophenyl)glycyl, (4-methoxyphenyl)glycyl, (4-methanesulfinylphenyl)glycyl, (3-methanesulfonamidophenyl)glycyl, 1-cyclohexenylglycyl, thienylglycyl, furylglycyl, cyclohexadienylglycyl, (3,4-dihydroxyphenyl)glycyl, etc.; 5-methyl-3-phenyl-4-isoxazolylcarbonyl; 3-(2,6-dichlorophenyl)-5-methyl-4-isoxazolylcarbonyl; and so forth. It should be understood that the above-mentioned groups are only illustrative of the acyl groups that are of use for the purposes of this invention, but preferable acyl groups may be represented by the formula:

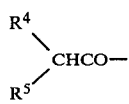

wherein R⁴ stands for acetyl, halogenoacetyl, phenyl, p-hydroxyphenyl, thienyl, 2-imino-4-thiazolin-4-yl, 2-oxo-4-thiazolin-4-yl, tetrazolyl, phenoxy, 3-amino-3-carboxypropyl, etc. and R⁵ stands for hydrogen, sulfo, amino, hydroxy, etc.

It should also be understood that any functional groups, e.g. amino or/and carboxyl, in such acyl groups may be suitably protected. Thus, among protective groups for said amino groups are aromatic acyl groups such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, etc.; aliphatic acyl groups such as acetyl, valeryl, capryl, n-decanoyl, acryloyl, camphorsulfonyl, methanesulfonyl, chloroacetyl, etc.; esterified carboxyl groups such as tert-butoxycarbonyl, ethoxycarbonyl, isobornyloxycarbonyl, phenyloxycarbonyl, trichloroethoxycarbonyl, benzyloxycarbonyl, β-methylsulfonylethoxycarbonyl, etc.; carbamoyl groups such as methylcarbamoyl, phenylcarbamoyl, naphthylcarbamoyl, etc.; the corresponding thiocarbamoyl groups; 2-methoxycarbonyl-1-methylvinyl; and so forth. As protective groups for the carboxyl groups of said acyls R¹ and the 4-carboxyl group of the cephem ring, there may be mentioned methyl, ethyl, tert-butyl, tert-amyl, benzyl, p-nitrobenzyl, p-methoxybenzyl, benzhydryl, 1-indanyl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, silyl groups such as trimethylsilyl, dimethylsilyl, etc.; and so forth. These carboxyl groups may also be in the form of inorganic or organic salts with alkali metals such as lithium, sodium, potassium, magnesium, etc.; alkaline earth metals such as calcium; or various amines such as dicyclohexylamine, triethylamine, tributylamine, di-n-butylamine, di-n-propylamine and so forth.

The organic residue denoted by X in said compound [I] is usually a carbon chain which is able to form a five- or six-membered ring with

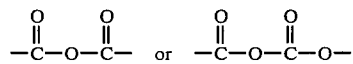

and which may include a double bond or such an atom or atoms as oxygen, nitrogen or sulfur therein, preferably oxygen. Moreover, the carbon chain may be such that its carbon atoms carry suitable substituent groups. Among examples of such substituents on the carbon chain, there may be mentioned carboxyl, halogen, nitro, alkyl (e.g. methyl, ethyl, propyl, methylene, ethylene), aralkyl (e.g. benzyl, phenethyl, etc.), aryl (e.g. phenyl, tolyl, etc.), and hydroxy or mercapto groups substituted thereby (e.g. methoxy, p-chlorophenylthio, etc.). Where two or more such substituents are present, they may form a ring with the carbon chain. Of those compounds [I], the compounds in which W is acetonyl can be produced by reacting a compound of the general formula:

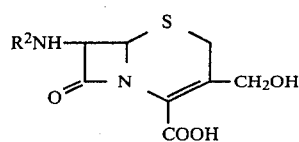

[wherein R² is hydrogen or an acyl group] with diketene. The diketene may be used as well in the form of an adduct with acetone, acetophenone or the like. This is an equimolar reaction, which means that the desired reaction can be accomplished by using [II] and diketene in equimolar proportions. However, to adjust for the possible decomposition of diketone which would take place in the presence of water or alcohol, an excess of diketene may be employed. Normally this reaction can be successfully conducted by allowing a 3-hydroxymethylcephalosporin [II] and diketene to interact in a suitable inert solvent at a temperature of $-30°$ C. to $40°$ C. As said suitable inert solvent, there may be employed any of such solvents as dichloromethane, chloroform, dichloroethane, dimethylformamide, dimethylacetamide, tetrahydrofuran, acetonitrile, ethyl acetate, acetone, dioxane, ether, etc. and various mixtures of such solvents. The reaction of diketene with 3-hydroxymethylcephalosporin [II] proceeds at a high rate, but in consideration of the fact that the reaction rate depends somewhat on the reaction temperature, and to ensure that the reaction will be carried to completion, this reaction is usually conducted for a period of 0.5 to 15 hours. If necessary, an amine such as triethylamine may be added to the reaction system, or where the starting material [II] is an alkali metal salt, an equivalent of, for example, triethylamine hydrochloride may be added to effect a salt interchange before the desired reaction takes place.

Where W stands for —X—COOH, the compound can be produced by reacting a 3-hydroxymethylcephalosporin [II] with a compound of the general formula:

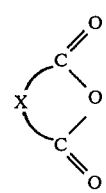

[where X has the same meaning as defined hereinbefore].

As specific examples of compound [III], there may be mentioned maleic anhydride, succinic anhydride, phthalic anhydride, glutaric anhydride, diglycolic anhydride, thiodiglycolic anhydride, p-chlorophenylthiosuccinic anhydride, methylenesuccinic anhydride, 3-nitrophthalic anhydride, trimellitic anhydride, isatoic anhydride.

Generally speaking, the reaction of compound [II] with compound [III] is expediently conducted in the presence of a suitable inert solvent like that used in the reaction described just above. The stoichiometric proportions of reactants, reaction temperature and other conditions of reaction may also be similar to those used for the reaction described.

The compound wherein W is —X—OH may be produced by reacting a 3-hydroxymethylcephalosporin [II] with a compound of the general formula:

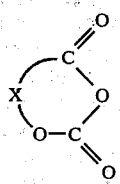 (IV)

[wherein X has the same meaning as defined hereinbefore].

Thus, as examples of compound [IV], there may be mentioned O-carboxymandelic anhydride, O-carboxy-α-hydroxypropionic anhydride, O-carboxy-β-hydroxypropionic anhydride, O-carboxy-3-methylsalicylic anhydride, O-carboxy-(α-hydroxy-α-phenyl)propionic anhydride, O-carboxy-(α-hydroxy-β-phenyl)propionic anhydride and so forth.

The conditions of reaction between compound [II] and compound [IV] are similar to those used for the reactions previously described. Where the starting material [II] has an unprotected amino group, the reaction thereof with diketene, compound [III] or compound [IV] may be conducted so that both the 3-hydroxy and the amino group may be simultaneously acylated by the same acyl groups.

The resultant compound [I] not only has antibiotic activity as such but is ready to react with a nucleophilic compound to introduce the residue of said nucleophilic compound into the 3-methyl group of the cephalosporin to give the compound represented by the formula:

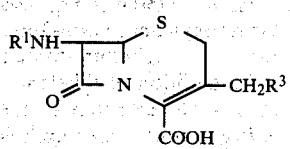

wherein R³ stands for a residue of a nucleophilic compound and R² has the same meaning as defined before. As to the nucleophilic compound used for this reaction, any of the compounds that are able to replace the 3-acetoxy groups of cephalosporins may be used. Furthermore, the reaction proceeds at a rate ranging from 4 to 16 times that of the 3-acetoxy compound and almost quantitatively.

Therefore, among such nucleophilic compounds are nitrogen-containing heterocyclic thiols which contain one or more nitrogen atoms which may optionally be in the form of oxide or/and which contain such atoms as oxygen or/and sulfur in addition to the nitrogen atom, with or without nuclear substitution. As the common examples of the nitrogen-containing heterocyclic group of such a thiol compound, there may be mentioned pyridyl, N-oxidepyridyl, pyrimidyl, pyridazinyl, N-oxidepyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and so forth. As the substituents on such nitrogen-containing heterocyclic groups, there may be mentioned such monovalent groups as hydroxy, mercapto, amino, carboxyl, carbamoyl, lower alkyl (for example, methyl, ethyl, trifluoromethyl, propyl, isopropyl, butyl, isobutyl, etc.), lower alkoxy (for example, methoxy, ethoxy, propoxy, isopropoxy, butoxy, etc.), halogens (e.g. chlorine, bromine, etc.), and various substituent groups as attached through lower alkylene groups, —S—, —N— or other polyvalent groups. When such polyvalent groups are lower alkylene groups, the substituents may for example be hydroxy, mercapto, amino, morpholino, carboxyl, sulfo, carbamoyl, alkoxycarbonyl, lower alkylcarbamoyl, alkoxy, alkylthio, alkylsulfonyl, acyloxy, morpholinocarbonyl and so forth. When such a polyvalent group is —S— or —N—, the substituents may be lower alkyls or lower alkylene groups having the aforementioned substituents. When the polyvalent group is —N—, such substituents as carboxyl, alkoxycarbonyl, acyl, carbamoyl, lower alkylcarbamoyl, etc. may be directly attached. More particularly, there may be mentioned substituted alkyl groups such as carboxymethyl, carbamoylmethyl, N-lower alkylcarbamoylmethyl (e.g. N,N-dimethylcarbamoylmethyl), hydroxy lower alkyl (e.g. hydroxymethyl, 2-hydroxyethyl), acyloxy lower alkyl (e.g. acetoxymethyl, 2-acetoxyethyl), alkoxycarbonylmethyl (e.g. methoxycarbonylmethyl, hexyloxycarbonylmethyl, octyloxycarbonylmethyl), methylthiomethyl, methylsulfonylmethyl, N-lower alkylamino lower alkyl (e.g. N,N-dimethylaminomethyl, N,N-dimethylaminoethyl, N,N,N-trimethylammoniumethyl), morpholinomethyl, etc.; substituted amino groups such as lower alkylamino (e.g. methylamino), sulfo-lower alkylamino (e.g. 2-sulfoethylamino), hydroxylower alkylamino (e.g. hydroxyethylamino), lower alkylamino-lower alkylamino (e.g. 2-dimethylaminoethylamino, 2-trimethylammoniumethylamino), acylamino (e.g. acetylamino), 2-dimethylaminoacetylamino, 2-trimethylammoniumacetylamino, lower alkoxycarbonylamino (e.g. methoxycarbonylamino), etc.; and substituted thio (mercapto) groups such as methylthio, 2-hydroxyethylthio, 2-acyloxyethylthio (e.g. 2-acetoxyethylthio, 2-phenylacetoxyethylthio, 2-caproyloxyethylthio), carboxymethylthio, alkoxycarbonylmethylthio (e.g. methoxycarbonylthio, hexyloxycarbonylmethylthio), carbamoylmethylthio, N-lower alkylcarbamoylmethylthio (e.g. N,N-dimethylcarbamoylmethylthio), acetylmethylthio, N-lower alkylamino-lower alkylthio (e.g. 2-N,N-dimethylaminoethylthio, 2-N,N,N-trimethylammoniumethylthio), morpholinocarbonylmethylthio, 2-sulfoethylthio and so forth. More particularly, there may be mentioned various heterocyclic thiols such as tetrazolethiol, methyltetrazolethiol, phenyltetrazolethiol, (2-N,N-dimethylaminoethyl)tetrazolethiol, methylthiadiazolethiol, hydroxyethylthiothiadiazolethiol, methylthiothiadiazolethiol, thiadiazolethiol, carbamoylaminothiadiazolethiol, carbamoylmethylthiothiadiazolethiol, thiazolethiol, methylthiazolethiol, carboxymethylthiazolethiol, triazolethiol, dimethyltriazolethiol, pyrazolethiol, ethoxycarbonylmethyltriazolethiol, imidazolethiol, methyloxadiazolethiol, pyridinethiol, pyrimidinethiol, methylpyridazinethiol, triazinethiol and so forth. In addition, use may also be made of aliphatic or aromatic thiols, e.g. methanethiol, ethanethiol, thiophenol, etc.; thiourea and its derivatives such as N-methylthiourea, N-methyl-N'-pyridylthiourea, etc.; thioamide derivatives such as thiosemicarbazide, thioacetamide, thiobenzamide, etc.; sodium thiosulfate, sodium sulfite, potassium thiocyanate, sodium azide, etc.; such nitrogen-containing heterocyclic compounds as pyridine and pyridine derivatives such as picoline, nicotinic acid, nicotinamide, isonicotinamide, isonicotinic acid hydrazide, m-bromopyridine, pyridinesulfonic acid, pyridine-m-carbinol (3-hydroxymethylpyridine), pyridinaldehyde, quinoline, isoquinoline, etc.; and such other nitrogen-containing heterocyclic compounds as pyrazine, pyrazinamide (2-carbamoylpyrazine), pyridazine, pyrimidine, imidazole, 1-methylimidazole, pyrazol and so forth. It is also possible to employ carbon nucleophilic agents toward which the 3-position is known to be refractory. As examples of such carbon nucleophilic reagents, there may be mentioned cyanides, pyrrole, substituted pyrrole, indole, acetylene, active methylene compounds, e.g. acetylacetone, acetoacetic acid esters, malonic acid esters, cyclohexane-1,3-dione, triacetylmethane and enamine compounds. Alcohols such as methanol, ethanol, propanol, etc. may also be employed in this reaction.

The substitution reaction between such a nucleophilic compound and a compound of formula [I] is normally conducted in a solvent. While the commonest solvent is water, the hydrophilic organic solvents inert to the reaction, e.g. acetone, tetrahydrofuran, dimethylformamide, methanol, ethanol, dimethylsulfoxide, etc., and aqueous solvents such as mixtures of water and such reaction-inert, polar solvents as mentioned above, are employed with preference.

While compound [I] may be a free compound, it is more advantageous to subject [I] to the reaction in the form of an alkali metal salt, e.g. the sodium, potassium or other salt, or an organic amine salt, e.g. the triethylamine, trimethylamine or other amine salt. The nucleophilic agent is also reacted in its free form or as an alkali metal, organic amine or other salt.

The proportion of the nucleophilic compound to be used in this reaction is preferably one equivalent or more with respect to compound [I]. While the optimum pH depends upon the particular nucleophilic compound and compound [I], the reaction is generally carried out under weakly acid to weakly alkaline conditions. The reaction temperature is preferably somewhere between 40° C. and 70° C., although there are no particular limits. The reaction time cannot be specified in general terms, either, for it depends upon the reaction temperature, pH, type of nucleophilic reagent and other factors. Roughly speaking, however, the reaction goes to completion in 30 minutes to 2 hours when the reaction temperature is 60° C. The reaction may also be carried out in the presence of, as added to the reaction system, an inorganic salt, e.g. the chloride, bromide, iodide, thiocyanide or nitrate of lithium, sodium, potassium, ammonium or the like.

The compound [I] wherein $R^1$ is an acyl group can be converted to the corresponding compound wherein $R^1$ is hydrogen by cleaving the 7-acyl group off in a manner conventional per se (e.g. any of the procedures set forth in Japanese Patent Publication No. 13862/1966 and No. 40899/1970, Japanese Patent Application Laid Open No. 34387/1972, No. 95292/1975 and No. 96591/1975, Japanese Patent Publication No. 35079/1975, U.S. Pat. No. 3,632,578, etc.).

Into this compound, where $R^1$ is hydrogen, may be introduced a compound which has previously been mentioned by way of example for $R^1$ as the 6- or 7-substituents of penicillin or cephalosporin compounds, by previously activating the same in a known manner. Thus, for example, the compound wherein $R^1$ is 4-halogeno-3-oxobutyryl can be obtained by reacting the compound where $R^1$ is hydrogen with a 4-halogeno-3-oxobutyryl halide which, in turn, may be reacted with thiourea to produce the 7-[2-(2-imino-4-thiazolin-4-yl)acetamido]compound. While it depends somewhat on the type of 3-substituent, these compounds invariably display excellent antibiotic activity. For example, the compound with 1-methyltetrazol-5-ylthiomethyl in 3-position is particularly useful, approximately the same effect being accomplished with this compound at a dose about one-fifth that of oephazolin.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g", "mg", "ml", "cm", "Hz", "DMSO", and "decomp." are abbreviations of "gram", "milligram", "milliliter", "centimeter", "Herz", "dimethylsulfoxide", and "decomposed", respectively. Resins named "Amberlite" are products manufactured by Rohm & Hars Co. in U.S.A. "Celite" and Sephadex are marketed by Johns-Manville Sales Corp. and Pharmacia A.B., respectively. All the temperatures are uncorrected and the percentages are all on the weight basis except as specifically defined. The NMR spectra given therein were measured using a Varian Model HA 100 (100 MHz) or T60 (60 MHz) spectrometer with tetramethylsilane as the internal reference and all δ values are in ppm. The symbol s stands for a singlet, d a doublet, t a triplet, q a quartet, m a multiplet, and J a coupling constant.

EXAMPLE 1

(1) In dichloromethane (50 ml) was dissolved 7β-[D-5-phthalimido-5-carboxyvaleramido]-3-hydroxymethyl-3-cephem-4-carboxylic acid ditriethylamine salt (7.05 g), followed by the addition of diketene (0.92 g). The reaction was carried out at room temperature for 3 hours. After the reaction had been completed, the solvent was distilled off under reduced pressure and the residue was diluted with water and adjusted to pH 6.0 with sodium hydrogen carbonate. The aqueous solution was washed twice with ethyl acetate, brought down to pH 2.0 with 4 N-HCl and extracted three times with ethyl acetate. The ethyl acetate solution was washed with a saturated aqueous solution of sodium chloride, treated with magnesium sulfate and filtered. The solvent was then distilled off under reduced pressure. To the residue was added ether and the resultant powder was collected by filtration, washed with ether and dried. The above procedure provided 7β-[D-5-phthalimido-5-carboxyvaleramido]-3-(3-oxobutyryloxy)methyl-3-cephem-4-carboxylic acid (5.48 g) (yield 93.2%).

IR(KBr): 3350, 1775, 1740, 1715, 1640, 1530 cm$^{-1}$.

NMR(δ in d$_6$-DMSO): 1.30–2.40(6H,m), 2.17(3H,s), 3.46(2H,ABq,J=18 Hz), 3.60(2H,s), 4.72(1H,t), 4.90(2H,ABq,J=12 Hz), 5.01(1H,d,J=5 Hz), 5.62(1H,dd,J=5 & 8 Hz), 7.88(4H,s), 8.80(1H,d,J=8 Hz).

(2) In water (50 ml) was dissolved 7β-[D-5-phthalimido-5-carboxyvaleramido]-3-(3-oxobutyryloxy)methyl-3-cephem-4-carboxylic acid (5.88 g), together with 5-mercapto-1-methyl-1H-tetrazole (1.50 g) and sodium hydrogen carbonate (2.10 g). Following the addition of sodium chloride (15.0 g), the solution was adjusted to pH 5.0 and, then, reacted at 60° C. for 50 minutes. After cooling, a saturated aqueous solution of sodium chloride (50 ml) was added and the mixture was adjusted to pH 1.5 with 4 N-HCl. The resultant solid precipitate was recovered by filtration, washed with a saturated aqueous solution of sodium chloride (20 ml) and dissolved in ethyl acetate (100 ml)-water (20 ml). After separation, the ethyl acetate solution was dried and, following the addition of toluene (50 ml), concentrated. The solid precipitate was recovered by filtration, washed with toluene-ether and dried. The procedure provided 7β-[D-5-phthalimido-5-carboxyvaleramido]-3-(1-methyl-1H-tetrazol-5-yl)thiomethyl-3-cephem-4-carboxylic acid (5.75 g) (yield 95.5%).

IR(KBr): 3325, 1780, 1730, 1715, 1650, 1545 $cm^{-1}$.

NMR($\delta$ in $d_6$-DMSO): 1.40–1.76(2H,m), 2.0–2.4(4H,m), 3.64(2H,ABq,J=19 Hz), 3.93(3H,s), 4.30(2H,ABq,J=15 Hz), 4.73(1H,t,J=8 Hz), 5.01(1H,d,J=5 Hz), 5.62(1H,dd,J=5 & 9 Hz), 7.85(4H,s), 8.80(d,J=9 Hz)

(3) In water (60 ml) was dissolved 7β-[D-5-phthalimido-5-carboxyvaleramido]-3-(3-oxobutyryloxy)methyl-3-cephem-4-carboxylic acid (5.88 g) together with 2-(2-hydroxyethylthio)-5-mercapto-1,3,4-thiadiazole (2.90 g) and sodium bicarbonate (2.20 g). Following the addition of sodium bromide (30 g), the solution was adjusted to pH 5.5 and reacted at 60° C. for 50 minutes. After the reaction was completed, the reaction mixture was diluted with water (40 ml) and adjusted to pH 5.0. The aqueous solution was washed twice with ethyl acetate, brought down to pH 2.0 with 4 N-HCl and extracted three times with a mixture of ethyl acetate and tetrahydrofuran (4:1). The organic layer was washed with a saturated aqueous solution of sodium chloride, dried over magnesium sulfate, filtered and distilled under reduced pressure to remove the solvent. To the residue was added ethyl acetate-ether and the resultant powder was recovered by filtration, washed with ether and dried. The procedure provided 7β-[D-5-phthalimido-5-carboxyvaleramido]-3-[2-(2-hydroxyethylthio)-1,3,4-thiadiazol-5-yl]thiomethyl-3-cephem-4-carboxylic acid (6.56 g) (yield 96.6%)

IR(KBr): 3325, 1780, 1715, 1645, 1530 $cm^{-1}$.

NMR($d_6$-DMSO): δ1.30–2.40(6H,m), 3.20–3.80(6H,m), 4.27(2H,ABq,J=12 Hz), 4.65(1H,t,J=9 Hz), 4.96(1H,d,J=5 Hz), 5.55(1H,dd,J=5 & 8 Hz), 7.87(4H,s), 8.70(1H,d,J=8 Hz).

(4) In a mixture of water (50 ml) and tetrahydrofuran (30 ml) was dissolved 7β-[D-5-phthalimido-5-carboxyvaleramido)-3-(3-oxobutyryloxy)methyl-3-cephem-4-carboxylic acid (5.88 g) together with 2-carbamoylmethylthio-5-mercapto-1,3,4-thiadiazole (2.28 g) and sodium bicarbonate (2.20 g). The solution was adjusted to pH 5.8 and, then, reacted at 60° C. for 70 minutes. After cooling, water (30 ml) was added and the aqueous solution was adjusted to pH 5.0, washed twice with ethyl acetate and brought down to pH 2.0 with 4 N-HCl. It was then extracted three times with a solvent mixture of ethyl acetate and tetrahydrofuran (2:1) and the organic layer was washed with a saturated aqueous solution of sodium chloride and dried over magnesium sulfate. The solvent was distilled off under reduced pressure and the residue was treated with ethyl acetate. The resultant powder was recovered by filtration, washed with ethyl acetate and dried. The procedure provided 7β-[D-5-phthalimido-5-carboxyvaleramido]-3-(2-carbamoylmethylthio-1,3,4-thiadiazol-5-yl)thiomethyl-3-cephem-4-carboxylic acid (5.83 g) (yield 84.2%).

IR(KBr): 3430, 3340, 1776, 1717, 1680, 1535 $cm^{-1}$.

NMR($d_6$-DMSO): δ 1.30–2.40(6H,m), 3.57(2H,br), 4.40(2H,s), 4.32(2H,ABq,J=12 Hz), 4.70(1H,t,J=8 Hz), 5.0(1H,d,J=5 Hz), 5.55(1H,dd,J=5 & 8 Hz), 7.20(1H,broad), 7.60(1H,broad), 7.86(4H,s), 8.74(1H,d,J=8 Hz).

EXAMPLE 2

(1) In dichloromethane (50 ml) was dissolved 7β-[D-5-benzamido-5-carboxyvaleramido]-3-hydroxymethyl-3-cephem-4-carboxylic acid ditriethylamine salt (6.69 g). At room temperature, triethylamine (1.01 g) and diketene (1.68 g) were added and the reaction was carried out for 3.0 hours. After the reaction had been completed, the reaction mixture was treated in the same manner as Example 1. The procedure provided 7β-[D-5-benzamido-5-carboxyvaleramido]-3-(3-oxobutyryloxy)methyl-3-cephem-4-carboxylic acid (5.12 g) (yield 91.3%).

IR(KBr): 3350, 1780, 1735, 1720, 1640, 1530 $cm^{-1}$.

NMR(δ in $d_6$-DMSO): 1.45–2.40(6H,m), 2.18(3H,s), 3.50(2H,ABq,J=19 Hz), 4.34(1H,m), 4.88(2H,ABq,J=13 Hz), 5.05(1H,d,J=5 Hz), 5.65(1H,dd,J=5 & 9 Hz), 7.27–8.0(5H,m), 8.46(1H,d,J=8 Hz), 8.75(1H,d,J=9 Hz).

(2) In water (20 ml) was dissolved 7-[D-5-benzamido-5-carboxyvaleramido]-3-(3-oxobutyryloxy)methyl-3-cephem-4-carboxylic acid (561 mg) together with potassium iodide (400 mg) and pyridine (212 mg). The solution was adjusted to pH 6.5 and, then, reacted at 60° C. for 50 minutes. Following the addition of water (10 ml), the aqueous solution was adjusted to pH 7.0, washed twice with dichloromethane (5.0 ml), readjusted to pH 6.0 and concentrated under reduced pressure. The residue was subjected to column chromatography on Amberlite XAD-2, followed by elution with water and, then, with a mixture of water and methanol. The eluate was concentrated and lyophilized. The procedure provided N-{7β-[D-5-benzamido-5-carboxyvaleramido]-3-cephem-3-ylmethyl}pyridinium-4-carboxylate monosodium salt (352 mg).

IR(KBr): 3360, 3250, 1765, 1645, 1630, 1605, 1575, 1530 $cm^{-1}$.

NMR($D_2O$): δ1.50–2.60(6H,m), 3.14(2H,ABq,J=19 Hz), 4.36(1H,m), 5.05(1H,d,J=5 Hz), 5.32(2H,ABq,J=15 Hz), 5.60(1H,dd,J=5 Hz), 7.0–9.0(10H,m).

(3) In water (6.0 ml) was dissolved 7-[D-5-benzamido-5-carboxyvaleramido]-3-(3-oxobutyryloxy)-methyl-3-cephem-4-carboxylic acid (561 mg) together with thiourea (100 mg) and sodium hydrogen carbonate (253 mg). The solution was adjusted to pH 6.5 and reacted at 60° C. for 50 minutes. After cooling, the reaction mixture was subjected to column chromatography on Amberlite XAD-2, followed by elution with water and water-methanol. The eluate was concentrated and lyophilized. The procedure provided S-{7-[D-5-benzamido-5-carboxyvaleramido]-3-cephem-3-ylmethyl}-thiouronium-4-carboxylate monosodium salt (464 mg).

IR(KBr): 3350, 3230, 1762, 1645, 1630, 1600, 1580, 1535 $cm^{-1}$.

NMR($D_2O$): δ1.50–2.50(6H,m), 3.20–3.80(3H,m), 4.40(2H, m), 5.05(1H,d,J=5 Hz), 5.53(1H,dd,J=5 Hz), 7.30–7.90(5H,m).

EXAMPLE 3

In dichloromethane (50 ml) was dissolved 7β-[D-5-(p-toluenesulfonamido)-5-carboxyvaleramido]-3-hydroxymethyl-3-cephem-4-carboxylic acid ditriethylamine salt (7.29 g) and, at room temperature, triethylamine (0.51 g) and diketene (1.26 g) were added. The reaction was carried out for 4.0 hours, after which time the reaction mixture was treated as in Example 1. The procedure provided 7β-[D-5-(p-toluenesulfonamido)-5-carboxyvaleramido]-3-(3-oxobutyryloxy)methyl-3-cephem-4-carboxylic acid (5.64 g) (yield 92.3%).

IR(KBr): 3275, 1780, 1740, 1730, 1715, 1640, 1535 cm$^{-1}$.

NMR(δ in d$_6$-DMSO): 1.30–1.80(4H,m), 2.0–2.4(2H,m), 2.16(3H,s), 2.33(3H,s), 3.45(2H,ABq,J=19 Hz), 4.91(2H,ABq,J=12 Hz), 5.0(1H,d,J=5 Hz), 5.57(1H,dd,J=5 & 8 Hz), 7.40(4H,m), 7.81(1H,d,J=9 Hz), 8.64(1H,d,J=8 Hz).

EXAMPLE 4

In dichloromethane (50 ml) was dissolved 7β-[D-5-tert-butylbenzamido)-5-carboxyvaleramido]-3-hydroxymethyl-3-cephem-4-carboxylic acid ditriethylamine salt (7.35 g) and, at room temperature, triethylamine (1.01 g) and diketene (1.68 g) were added. The reaction was carried out for 2 hours, after which time the reaction mixture was treated as in Example 1. The procedure provided 7β-[D-5-(p-tert-butylbenzamido)-5-carboxyvaleramido]-3-(3-oxobutyryloxy)methyl-3-cephem-4-carboxylic acid (5.78 g) (yield 93.8%).

IR(KBr): 3280, 1780, 1740, 1725, 1710, 1640, 1530 cm$^{-1}$.

NMR(δ in d$_6$-DMSO): 1.32(9H,s), 1.50–2.40(6H,m), 2.18(3H,s), 3.48(2H,br), 3.57(2H,s), 4.35(1H,m), 4.94(2H,ABq,J=13 Hz), 5.06(1H,d,J=5 Hz), 5.62(1H,dd,J=5 & 8 Hz), 7.46(2H, d,J=8 Hz), 7.85(2H,d,J=8 Hz), 8.35(1H,d,J=8 Hz), 8.78(1H,d,J=8 Hz).

EXAMPLE 5

In dichloromethane (50 ml) was dissolved 7β-[D-5-caprylamido-5-carboxyvaleramido]-3-hydroxymethyl-3-cephem-4-carboxylic acid ditriethylamine salt (6.01 g), followed by the addition of triethylamine (1.01 g) and diketene (1.68 g). The reaction was carried out at room temperature for 3 hours, after which time the reaction mixture was treated as in Example 1. The procedure provided 7β-[D-5-caprylamido-5-carboxyvaleramido]-3-(3-oxobutyryloxy)methyl-3-cephem-4-carboxylic acid (4.36 g) (yield 90.3%).

IR(KBr): 3320, 1780, 1745, 1725, 1715, 1645, 1535 cm$^{-1}$.

NMR(δ in d$_6$-DMSO): 0.70–2.40(2 1H,m), 2.22(3H,s), 3.53(2H,broad), 3.60(2H,s), 4.18(1H,m), 4.91(2H,ABq,J=12 Hz), 5.04(1H,d,J=5 Hz), 5.65(1H,dd,J=5 & 8 Hz), 7.87(1H,d,J=8 Hz), 8.70(1H,d,J=8 Hz).

EXAMPLE 6

In dichloromethane (50 ml) was dissolved 7β-phenylacetamido-3-hydroxymethyl-3-cephem-4-carboxylic acid triethylamine salt (4.49 g) and, at room temperature, triethylamine (0.51 g) and diketene (1.26 g) were added. The reaction was conducted for 2 hours, after which time the solvent was distilled off under reduced pressure. The residue was diluted with water and adjusted to pH 6.0. This aqueous solution was extracted twice with ethyl acetate, brought down to pH 2.0 with 4 N-HCl and extracted three times with ethyl acetate. The ethyl acetate solution was washed with a saturated aqueous solution of sodium chloride, treated with magnesium sulfate and filtered. The solvent was distilled off under reduced pressure and the residue was recrystallized from ethyl acetate-ether. The above procedure provided 7β-phenylacetamido-3-(3-oxobutyryloxy)methyl-3-cephem-4-carboxylic acid (4.16 g) (yield 96.3%).

IR(KBr): 3270, 1785, 1745, 1715, 1655, 1540 cm$^{-1}$.

NMR(δ in d$_6$-DMSO): 2.14(3H,s), 3.52(6H,broad), 4.86(2H,ABq,J=13 Hz), 5.00(1H,d,J=5 Hz), 5.63(1H,dd,J=5 & 9Hz), 7.22(5H,s), 8.93(1H,d,J=9 Hz).

EXAMPLE 7

A mixture of dichloromethane (300 ml), triethylamine (27 ml) and dimethylaniline (100 ml) was previously cooled to 10° C., and 7-[D-5-phthalimido-5-carboxyvaleramido]-3-(1-methyl-1H-tetrazol-5-yl)thiomethyl-3-cephem-4-carboxylic acid (50 g) was dissolved therein. To this solution was added dichlorodimethylsilane (36 ml) whereupon the internal temperature increased to 27° C. The mixture was stirred at that temperature for 30 minutes, after which time the internal temperature was brought down to −35° C. Then, phosphorus pentachloride (32.4 g) was added. The mixture was stirred at −25° C. for 40 minutes and, after cooling to −35° C., thioacetamide (20 g) was added. The mixture was further stirred at −20°−−25° C. for 40 minutes and, after cooling to −30° C., methanol (200 ml) was gently added in droplets. Then, at the same temperature, sulfur monochloride (17 ml) was gently added dropwise. The mixture was stirred for 20 minutes, after which time it was diluted with water (200 ml) and brought to pH 3.2 with 40% aqueous potassium carbonate solution. After stirring for 60 minutes, the resultant crystals were collected by filtration and rinsed with water and acetone. The crude crystals thus obtained were suspended in 10% hydrochloric acid (230 ml) and stirred at 30° C. for 1 hour. The insolubles were filtered off and the filtrate was cooled to 5°–10° C. and brought to pH 3.3 with potassium carbonate. The filtrate was stirred for one hour, then the precipitated crystals were collected by filtration, rinsed with water and acetone, and dried over phosphorus pentoxide. The procedure provided 7-amino-3-(1-methyltetrazol-5-yl)thiomethyl-3-cephem-4-carboxylic acid (17.0 g).

IR(KBr): 1795 cm$^{-1}$.

NMR(δ in D$_2$O-NaHCO$_3$): 3.61 & 3.98(ABq,J=18 Hz, 2-CH$_2$), 4.21(s,tetrazole-CH$_3$), 5.21(d,J=4.5 Hz,6-H), 5.60(d,J=4.5 Hz,7-H).

Chlorine gas (2.8 g) was bubbled through a solution of diketene (3.3 g) in methylene chloride (160 ml) under stirring and cooling to maintain the internal temperature at −25° to −35° C. for a period of 100 minutes. Then, the mixture was further stirred at the same temperature for 30 minutes. Separately, 7-amino-3-(1-methyltetrazol-5-yl)thiomethyl-3-cephem-4-carboxylic acid (10.0 g) and dibutylamine (7.9 g) were dissolved in methylene chloride (60 ml) and the solution was cooled to −10° C. To this solution, the above reaction mixture was added dropwise under stirring and cooling to maintain an internal temperature of −10° to −20° C. for 30 minutes. The mixture was further stirred at that temperature for 40 minutes. Thin-layer chromatography of this reaction mixture revealed the presence of 7-(4-chloro-3- oxobutylamido)-3-(1-methyltetrazol-5-yl)thiomethyl-3-cephem-4-carboxylic acid. Thiourea (4.64 g) was dissolved in this reaction mixture and the internal temperature was increased to 17°-19° C. The mixture was stirred at this temperature, whereupon crystals separated out. The crystals were recovered by suction-filtration, washed with methylene chloride (30 ml) and dried. The procedure provided the [2-(2-imino-4-thiazolin-4-yl)acetamido]-3-(1-methyltetrazol-5-yl)thiomethyl-3-cephem-4-carboxylic acid (12.8 g), melting point: 176°-180° C. (decomp.).

IR(KBr): 1762, 1662 cm$^{-1}$.

NMR($\delta$ in d$_6$-DMSO): 3.39(s,CH$_2$CO), 3.55 & 3.77(ABq,J=18 Hz,2-CH$_2$), 3.90(s,tetrazole 1-CH$_3$), 4.21 & 4.36(ABq,J=14 Hz,3-CH$_2$), 5.03(d,J=5 Hz,6-H), 5.66(dd,J=9 & 5Hz,7-H), 6.23(s,thiazolin 5-H),

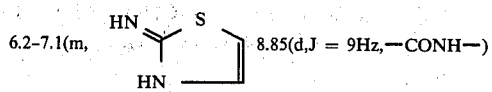 8.85(d,J = 9Hz,—CONH—)

EXAMPLE 8

In dichloromethane (30 ml) was dissolved 7$\beta$-(2-thienylacetamido)-3-hydroxymethyl-3-cephem-4-carboxylic acid triethylamine salt (4.55 g), followed by the addition of succinic anhydride (1.50 g). The mixture was stirred at room temperature for 2 hours. The dichloromethane was distilled off and, following the addition of 3% aqueous phosphoric acid solution (100 ml), the residue was extracted with ethyl acetate (150 ml). The ethyl acetate layer was washed with a saturated aqueous solution of sodium chloride (100 ml×2), dried (over magnesium sulfate) and concentrated under reduced pressure. The residue was treated with ether and the resultant powder was recovered by filtration, washed with ether and dried under reduced pressure over phosphorus pentoxide. The procedure provided 7$\beta$-(2-thienylacetamido)-3-(3-carboxypropionyloxy)methyl-3-cephem-4-carboxylic acid (4.00 g).

IR(KBr): 1782($\beta$-lactam), 1733(—CO$_2$H) cm$^{-1}$.

NMR($\delta$ in d$_6$-DMSO): 2.50(4H,—CO(CH$_2$)$_2$—), 3.40 & 3.63(2H,ABq,J=18 Hz,2—CH$_2$), 3.75(2H,s,—C$\underline{H}$$_2$CONH—), 4.71 & 5.07(2H,ABq,J=13 Hz,3-CH$_2$), 5.07(1H,d,J=5 Hz,6-H), 5.68(1H,dd,J=5 & 8 Hz,7-H),

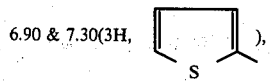

9.10(1H,d,J=8 Hz,—CONH—).

EXAMPLE 9

In dichloromethane (25 ml) was dissolved 7$\beta$-(2-thienylacetamido)-3-hydroxymethyl-3-cephem-4-carboxylic acid triethylamine salt (3.60 g), followed by addition of phthalic anhydride (1.80 g). The mixture was stirred at room temperature for 2 hours, after which time it was treated in a manner similar to that described in Example 8. The procedure provided 7$\beta$-(2-thienylacetamido)-3-(2-carboxybenzoyloxy)methyl-3-cephem-4-carboxylic acid (3.44 g).

IR(KBr): 1777, 1724, 1650(shoulder) cm$^{-1}$.

NMR($\delta$ in d$_6$-DMSO): 3.50 & 3.70(2H,ABq,J=18 Hz,2-CH$_2$), 3.77(2H,s,—CH$_2$CO—), 4.91 & 5.29(2H,ABq,J=13 Hz,3—CH$_2$), 5.10(1H,d,J=5 Hz,6-H), 5.70(1H,dd,J=5 & 8 Hz,7-H),

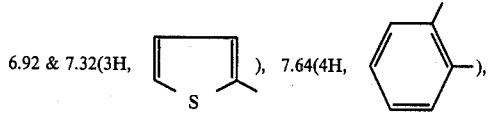

9.12(1H,d,J=8 Hz,—CONH—).

EXAMPLE 10

In dichloromethane (40 ml) was dissolved 7$\beta$-mandelamido-3-hydroxymethyl-3-cephem-4-carboxylic acid triethylamine salt (4.65 g), followed by addition of succinic anhydride (1.50 g). The mixture was stirred at room temperature for 1 hour and a half. After the reaction had been completed, the mixture was treated as in Example 8 to obtain 7$\beta$-mandelamido-3-(3-carboxypropionyloxy)methyl-3-cephem-4-carboxylic acid (4.45 g).

IR(KBr): 1776, 1737, 1684(shoulder) cm$^{-1}$.

NMR($\delta$ in d$_6$-DMSO): 2.48(4H,—CO(CH$_2$)$_2$—), 3.3-3.7(2H,2—CH$_2$), 4.69 & 5.03(2H,ABq,J=13 Hz,3-CH$_2$),

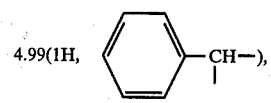

5.06(1H,d,J=5 Hz,6-H), 5.68(1H,dd,J=5 & 8 Hz,7-H),

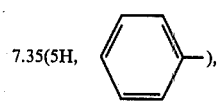

9.31(1H,d,J=8 Hz,—CONH—).

EXAMPLE 11

In dichloromethane (7 ml) was dissolved 7$\beta$-(2-thienylacetamido)-3-hydroxymethyl-3-cephem-4-carboxylic acid triethylamine salt (0.68 g), followed by addition of glutaric anhydride (0.34 g). The mixture was stirred at room temperature for 2 and a half hours. The dichloromethane was distilled off and, following the addition of 3% aqueous phosphoric acid (15 ml), the residue was extracted with ethyl acetate (25 ml). The ethyl acetate layer was washed with a saturated aqueous solution of sodium chloride (15 ml×2) and dried (over magnesium sulfate). Then, upon dropwise addition of a 2 N-solution of sodium 2-ethylhexanoate in isopropyl alcohol (1.50 ml), there was obtained a powder. This powder was recovered by filtration, washed with ethyl acetate-ether and dried over phosphorus pentoxide. The procedure provided 7$\beta$-(2-thienylacetamido)-3-(4-carboxybutyryloxy)methyl-3-cephem-4-carboxylic acid disodium salt (0.42 g).

IR(KBr): 1760, 1736(shoulder), 1661, 1609 cm$^{-1}$.

NMR($\delta$ in D$_2$O): 1.90(2H,—CH$_2$C$\underline{H}$$_2$CH$_2$—), 2.28(4H,—C$\underline{H}$$_2$CH$_2$C$\underline{H}$$_2$—), 3.21 & 3.61(2H,ABq,J=18 Hz,2-CH$_2$), 3.78(2H,s, 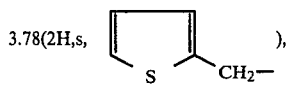), 4.4–4.9(2H,3—CH₂), 4.98(1H,d,J=5 Hz,6-H), 5.60(1H,d,J=5 Hz,7-H), 6.95 & 7.28(3H, 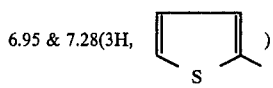)

EXAMPLE 12

In dimethylformamide (50 ml) was dissolved 7β-[D-5-(p-t-butylbenzamido)-5-carboxyvaleramido]-3-hydroxymethyl-3-cephem-4-carboxylic acid ditriethylamine salt (7.35 g), followed by addition of succinic anhydride (1.50 g). The mixture was stirred at room temperature for 30 minutes. After the reaction had been completed, 3% aqueous phosporic acid (250 ml) was added, followed by extraction with ethyl acetate (500 ml). The ethyl acetate layer was washed with water (250 ml×2), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7β-[D-5-(p-t-butylbenzamido)-5-carboxyvaleramido]-3-(3-carboxypropionyloxy)methyl-3-cephem-4-carboxylic acid (6.20 g).

IR(KBr): 1779, 1732, 1640 cm⁻¹.
NMR(δ in d₆-DMSO):

1.28(9H,s, 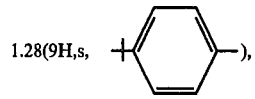), 1.73 & 2.24(6H,—(CH₂)₃—), 2.50(4H,—COCH₂CH₂CO—), 3.38 & 3.63(2H,ABq,J=18 Hz,2-CH₂), 4.37(1H,—CH-NH—), 4.71 & 5.06(2H,ABq,J=13 Hz,3-CH₂), 5.04(1H,d,J=5 Hz,6-H), 5.66(1H,dd,J=5 & 8 Hz,7-H), 7.44 & 7.81(4H, 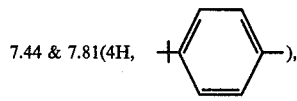), 8.43(1H,d,J = 8Hz, 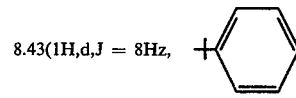—CONH—), 8.80(1H,d,J=8 Hz,—CONH—).

EXAMPLE 13

In dimethylformamide (50 ml) was dissolved 7β-[D-5-(p-t-butylbenzmido)-5-carboxyvaleramido]-3-hydroxymethyl-3-cephem-4-carboxylic acid ditriethylamine salt (7.35 g), followed by addition of phthalic anhydride (1.63 g). The mixture was stirred at room temperature for 30 minutes, after which time it was treated as in Example 12. The procedure provided 7β-[D-5-(p-t-butylbenzamido)-5-carboxyvaleramido]-3-(2-carboxybenzoyloxy)methyl-3-cephem-4-carboxylic acid (6.70 g).

IR(KBr): 1784, 1726, 1642 cm⁻¹.
NMR (δ in d₆-DMSO):

1.27(9H,s, 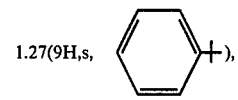), 1.72 & 2.22(6H,—(CH₂)₃—), 3.46 & 3.71(2H,ABq,J=18 Hz,2-CH₂), 4.37(1H,—CH—NH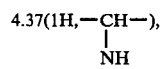), 4.89 & 5.27(2H,ABq,J=13 Hz,3—CH₂), 5.08(1H,d,J=5 Hz,6-H), 5.67(1H,dd,J=5 & 8 Hz,7-H), 7.43 & 7.81(4H, 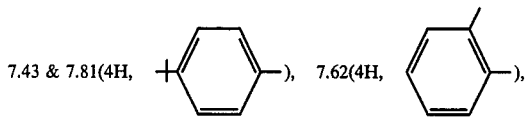), 7.62(4H, 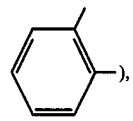), 8.42(1H,d,J=8 Hz,—CHNHCO—), 8.80(1H,d,J=8 Hz,—CONH—).

EXAMPLE 14

In dimethylformamide (50 ml) was dissolved 7β-[D-5-(p-t-butylbenzamido)-5-carboxyvaleramido]-3-hydroxymethyl-3-cephem-4-carboxylic acid ditriethylamine salt (7.35 g), followed by addition of maleic anhydride (1.49 g). The mixture was stirred at room temperature for 30 minutes, after which time it was treated as in Example 12. The procedure provided 7β-[D-5-(p-t-butylbenzamido)-5-carboxyvaleramido]-3-(3-carboxyacryloyloxy)methyl-3-cephem-4-carboxylic acid (6.05 g).

IR(KBr): 1780, 1727, 1640 cm⁻¹.
NMR(δ in d₆-DMSO):

1.32(9H,s, 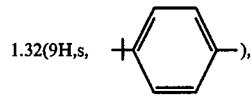), 1.77 & 2.26(6H,—(CH₂)₃—), 3.41 & 3.65(2H,ABq,J=18 Hz,2-CH₂), 4.37(1H, —CH— NH 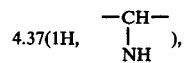), 4.80 & 5.16(2H,ABq,J=13 Hz,3—CH₂), 5.02(1H,d,J=5 Hz,6-H), 5.66(1H,dd,J=5 & 8 Hz,7-H), 6.34(2H,—CH=CH—), 7.44 & 7.82(4H, 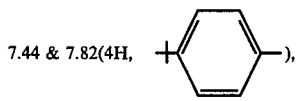), 8.40(1H,d,J=8 Hz,—CHNHCO—), 8.80(1H,d,J=8 Hz,—CONH—).

EXAMPLE 15

In dichloromethane (20 ml) was dissolved 7β-[D-5-(p-t-butylbenzamido)-5-carboxyvaleramido]-3-hydroxymethyl-3-cephem-4-carboxylic acid ditriethylamine salt (1.47 g), followed by addition of p-chlorophenylthiosuccinic anhydride (0.51 g). The mixture was stirred at room temperature for 1 hour, after which time it was treated as in Example 8. The procedure provided 7β-[D-5-(p-t-butylbenzamido)-5-carboxyvaleramido]-3-(3-carboxy-3(or 2)-(p-chlorophenylthio)propionyloxy)methyl-3-cephem-4-carboxylic acid (1.50 g).

IR(KBr): 1778, 1728, 1636 cm$^{-1}$.
NMR(δ in d$_6$-DMSO):

1.28(9H,s, 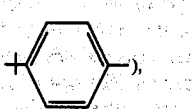), 1.74 & 2.24(6H,—(CH$_2$)$_3$—), 2.73(2H,—CH$_2$CH—),
        |
        S—

3.3–3.8(2H,2—CH$_2$), 4.03(1H,—CH—S),
        |

4.40(1H,—CH—NH—), 4.73 & 5.07(2H,ABq,J=13 Hz,3-CH$_2$), 5.02(1H,d,J=5 Hz,6-H), 5.68(1H,dd,J=5 & 8 Hz,7-H), 7.42(4H,Cl—⟨phenyl⟩—S—), 7.44 & 7.82(4H, +⟨phenyl⟩), 8.44(1H,d,J=8 Hz,—CHNHCO—), 8.82(1H,d,J=8 Hz,—CONH—).

EXAMPLE 16

In dichloromethane (50 ml) was dissolved 7β-(D-5-phthalimido-5-carboxyvaleramido)-3-hydroxymethyl-3-cephem-4-carboxylic acid ditriethylamine salt (7.05 g), followed by addition of succinic anhydride (1.50 g). The mixture was stirred at room temperature for 1 hour and a half, after which time it was treated as in Example 8. The procedure provided 7β-(D-5-phthalimido-5-carboxyvaleramido)-3-(3-carboxypropionyloxy)methyl-3-cephem-4-carboxylic acid (5.43 g).

IR(KBr): 1777, 1710, 1644 cm$^{-1}$.
NMR(δ in d$_6$-DMSO): 1.52 & 2.17(6H,—(CH$_2$)$_3$—), 2.50(4H,—(CH$_2$)$_2$—), 3.3–3.8(2H,2-CH$_2$), 4.70 & 5.03(2H,ABq,J=13 Hz,3-CH$_2$), 4.72(1H,t,J=7Hz, —CH—),
        |

5.01(1H,d,J=5 Hz,6-H), 5.62(1H,dd,J=5 & 8 Hz,7-H), 7.86(4H,s, ⟨phenyl⟩), 8.78(1H,d,J=8 Hz,—CONH—).

EXAMPLE 17

In dichloromethane (50 ml) was dissolved 7β-(D-5-phthalimido-5-carboxyvaleramido)-3-hydroxymethyl-3-cephem-4-carboxylic acid ditriethylamine salt (7.05 g), followed by addition of phthalic anhydride (2.22 g). The mixture was stirred at room temperature for 1 hour and a half, after which time it was treated as in Example 8. The procedure provided 7β-(D-5-phthalimido-5-carboxyvaleramido)-3-(2-carboxybenzoyloxy)methyl-3-cephem-4-carboxylic acid (6.39 g).

IR(KBr): 1772, 1714, 1643 cm$^{-1}$.
NMR(δ in d$_6$-DMSO): 1.52 & 2.18(6H,—(CH$_2$)$_3$—), 3.42 & 3.69(2H,ABq,J=18 Hz,2-CH$_2$), 4.74(1H,t,J=8Hz, —CH—),
        |

4.89 & 5.28(2H,ABq,13 Hz,3-CH$_2$), 5.06(1H,d,J=5 Hz,6-H), 5.66(1H,dd,J=5 & 8 Hz,7-H), 7.64(4H, ⟨phenyl⟩), 7.86(4H,s, ⟨phthalimido⟩N—), 8.81(1H,d,J=8 Hz,—CONH—).

EXAMPLE 18

7β-(2-Thienylacetamido)-3-(3-carboxyacryloyloxy)methyl-3-cephem-4-carboxylic acid was synthesized as in Example 8.

IR(KBr): 1780, 1725, 1638 cm$^{-1}$.
NMR(d$_6$-DMSO): δ 3.43 & 3.76(2H,ABq,J=18 Hz,2-CH$_2$), 3.75(2H,s,—CH$_2$CO—), 4.79 & 5.14(2H,ABq,J=13 Hz,3-CH$_2$), 5.07(1H,d,J=5 Hz,6-H), 5.68(1H,dd,J=5 & 8 Hz,7-H), 6.35(2H,s,—CH=CH—), 6.90 & 7.29(3H, 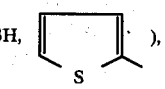), 9.10(1H,d,J=8 Hz,—CONH—).

EXAMPLE 19

To a mixture of 7β-[D-5-(p-t-butylbenzamido)-5-carboxyvaleramido]-3-hydroxymethyl-3-cephem-4-carboxylic acid ditriethylamine salt (2.20 g) and 3-nitrophthalic anhydride (1.16 g) was added dichloromethane (15 ml) together with triethylamine (0.42 ml). The resultant solution was stirred at room temperature for 1 hour and a half. After the reaction had been completed, the dichloromethane was distilled off under reduced pressure and 3% aqueous phosphoric acid (120 ml) and ethyl acetate (160 ml) were added to the residue. The ethyl acetate layer was washed with water (80 ml×2), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7β-[D-5-(p-t-butylbenzamido)-5-carboxyvaleramido]-3-(2-carboxy-6 (or 3)-nitrobenzoyloxy)-methyl-3-cephem-4-carboxylic acid (2.10 g).

IR(KBr): 1783, 1735, 1640 cm$^{-1}$.

NMR(δ in d$_6$-DMSO): 1.28(9H,s,—C(CH$_3$)$_3$), 1.53 & 2.23(6H,—(CH$_2$)$_3$—), 3.43 & 3.70(2H,ABq,J=18 Hz,2-CH$_2$), 4.37(1H, —CH—), 4.96 & 5.41(2H,ABq,J=13 Hz,3-CH$_2$), 5.07(1H,d,J=5 Hz,6-H), 5.68(1H,dd,J=5 & 8 Hz,7-H), 7.42 & 7.80(4H, 7.8–8.4(3H, 8.44(1H,d,J=8Hz, —CH—NH—), 8.84(1H,d,J=8 Hz,—CONH—).

EXAMPLE 20

To a mixture of 7β-(D-5-phthalimido-5-carboxyvaleramido)-2-hydroxymethyl-3-cephem-4-carboxylic acid ditriethylamine salt (2.12 g) and 3-nitrophthalic anhydride (1.16 g) was added dichloromethane (15 ml) together with triethylamine (0.42 ml). The solution was stirred at room temperature for 1 hour and a half, after which time it was treated as in Example 19. The procedure provided 7β-(D-5-phthalimido-5-carboxyvaleramido)-3-(2-carboxy-6 (or 3)-nitrobenzoyloxy)-methyl-3-cephem-4-carboxylic acid (2.08 g).

IR(KBr): 1775(shoulder), 1718, 1642 cm$^{-1}$.

NMR(δ in d$_6$-DMSO): 1.54 & 2.19(6H,—(CH$_2$)$_3$—), 3.40 & 3.68(2H,ABq,J=18 Hz,2-CH$_2$), 4.73(1H,t,J=7Hz, —CH—), 4.98 & 5.42(2H,ABq,J=13 Hz,3-CH$_2$), 5.06(1H,d,J=5 Hz,6-H), 5.66(1H,dd,J=5 & 8 Hz,7-H), 7.7–8.4(3H,

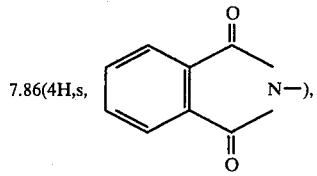
7.86(4H,s, 8.81(1H,d,J=8 Hz,—CONH—).

EXAMPLE 21

To 7β-[D-5-(p-t-butylbenzamido)-5-carboxyvaleramido]-3-hydroxymethyl-3-cephem-4-carboxylic acid ditriethylamine salt (2.20 g) and trimetallic anhydride (1.15 g) were added dichloromethane (15 ml) and triethylamine (0.84 ml) and the resultant solution was stirred at room temperature for 1 hour. After the reaction had been completed, the mixture was treated in the same manner as Example 19. The procedure provided 7β-[D-5-(p-t-butylbenzamido)-5-carboxyvaleramido]-3-(2,4 (or 5)-dicarboxybenzoyloxy)methyl-3-cephem-4-carboxylic acid (2.14 g).

IR(KBr): 1777, 1724, 1636 cm$^{-1}$.

NMR(δ in d$_6$-DMSO): 1.29(9H,s,—C(CH$_3$)$_3$), 1.54 & 2.25(6H,—(CH$_2$)$_3$—), 3.99 & 3.72(2H,ABq,J=18 Hz,2—CH$_2$), 4.38(1H, —CH—), 4.95 & 5.30(2H,ABq,J=13 Hz,3-CH$_2$), 5.11(1H,d,J=5 Hz,6-H), 5.70(1H,dd,J=5 & 8 Hz,7-H), 7.43 & 7.82(4H, 7.7–8.3(3H, 8.43(1H,d,J=8Hz, —CH—NH—), 8.84(1H,d,J=8 Hz,—CONH—).

EXAMPLE 22

In dimethylformamide (10 ml) was suspended desacetylcephalosporin C(2.16 g) and, under cooling with ice, concentrated hydrochloric acid (0.83 ml) was added. To the resultant solution was added dimethylformamide (10 ml) together with triethylamine (4.20 ml) and 3-nitrophthalic anhydride (3.86 g), and the mixture was stirred at room temperature for 2 hours. Following this reaction, the mixture was diluted with 3% aqueous phosphoric acid (150 ml) and extracted with ethyl acetate (250 ml×2). The ethyl acetate layer was washed with water (200 ml) and a saturated aqueous solution of sodium chloride (200 ml), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7β-[D-5-(2-carboxy-6 (or 3)-nitrobenzamido)-5-carboxyvaleramido)-3-

(2-carboxy-6(or 3)-nitrobenzoyloxy)methyl-3-cephem-4-carboxylic acid (3.77 g).

IR(KBr): 1780(shoulder), 1729, 1638, 1534, 1348 cm$^{-1}$.

NMR($\delta$ in d$_6$-DMSO): 1.67 & 2.23(6H,—(CH$_2$)$_3$—), 3.60(2H,2—CH$_2$), 4.39(1H, —CH—), 4.97 & 5.40(2H,ABq,J=13 Hz,3—CH$_2$), 5.08(1H,d,J=5 Hz,6-H), 5.68(1H,dd,J=5 & 8 Hz,7-H),

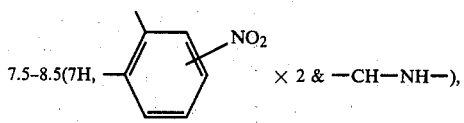

7.5–8.5(7H, ×2 & —CH—NH—), 8.78(1H,d,J=8 Hz,—CONH—).

EXAMPLE 23

In dichloromethane (30 ml) was dissolved 7$\beta$-(2-thienylacetamido)-3-hydroxymethyl-3-cephem-4-carboxylic acid triethylamine salt (4.55 g), followed by addition of O-carboxymandelic anhydride (2.38 g). The mixture was stirred at room temperature for 1 hours, after which time the dichloromethane was distilled off. To the residue was added 3% aqueous phosphoric acid (100 ml, followed by extraction with ethyl acetate (150 ml). The ethyl acetate layer was washed with a saturated aqueous solution of sodium chloride (100 ml×2), dried (over magnesium sulfate) and concentrated under reduced pressure. Then, upon addition of ether, there was obtained a powder. This powder was recovered by filtration, washed with ether and dried over phosphorus pentoxide under reduced pressure. The procedure provided 7$\beta$-(2-thienylacetamido)-3-mandelyloxymethyl-3-cephem-4-carboxylic acid (4.00 g).

IR(KBr): 1778, 1742, 1666 cm$^{-1}$.

NMR($\delta$ in d$_6$-DMSO): 3.24 & 3.45(2H,ABq,J=18 Hz,2-CH$_2$), 3.74(2H,s,—CH$_2$CONH—), 4.76 & 5.06(2H,ABq,J=13 Hz,3-CH$_2$), 5.03(1H,d,J=5 Hz,6-H),

5.16(1H,s, —CH—), 5.68(1H,dd,J=5 & 8 Hz,7-H),

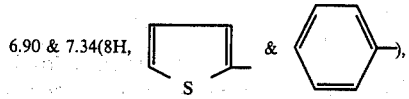

6.90 & 7.34(8H, & ), 9.09(1H,d,J=8 Hz,—CONH—).

EXAMPLE 24

In dimethylformamide (40 ml) was dissolved sodium 7$\beta$-mandelamido-3-hydroxymethyl-3-cephem-4-carboxylate (3.86 g), followed by addition of O-carboxymandelic anhydride (2.67 g). The mixture was stirred at room temperature for 30 minutes, after which 2% H$_3$PO$_4$(150 ml) was added. The mixture was extracted with ethyl acetate (250 ml) and the ethyl acetate layer was rinsed with water (150 ml×2), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7$\beta$-mandelamido-3-mandelyloxymethyl-3-cephem-4-carboxylic acid (3.68 g).

IR(KBr): 1777, 1745, 1669 cm$^{-1}$.

NMR($\delta$ in d$_6$-DMSO): 3.2–3.7(2H,2-CH$_2$), 4.7–5.2(5H,3-CH$_2$,6-H & —CH—×2), 5.69(1H,7-H),

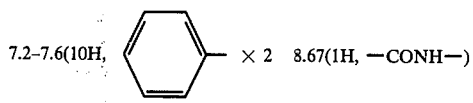

7.2–7.6(10H, ×2   8.67(1H, —CONH—)

EXAMPLE 25

In dimethylformamide (50 ml) was dissolved 7$\beta$-[D-5-(p-t-butylbenzamido)-5-carboxyvaleramido)-3-hydroxymethyl-3-cephem-4-carboxylic acid ditriethylamine salt (7.35 g), followed by the addition of O-carboxymandelic anhydride (2.67 g). The mixture was stirred at room temperature for 30 minutes, after which time 3% aqueous phosphoric acid (250 ml) was added, followed by extraction with ethyl acetate (500 ml). The ethyl acetate layer was rinsed with water (250 ml×2), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7$\beta$-[D-5-(p-t-butylbenzamido)-5-carboxyvaleramido)-3-mandelyloxymethyl-3-cephem-4-carboxylic acid (6.30 g).

IR(KBr): 1778, 1736, 1642 cm$^{-1}$.

NMR($\delta$ in d$_6$-DMSO): 1.29(9H,s,—C(CH$_3$)$_3$), 1.73 & 2.23(6H,—(CH$_2$)$_3$—), 3.2–3.6(2H,2—CH$_2$), 4.38(1H,—CH—NH—), 4.75 & 5.04(2H,ABq,J=13 Hz,3-CH$_2$), 5.02(1H,d,J=5 Hz,6-H),

5.16(1H,s, —CH—), 5.66(1H,dd,J=5 & 8 Hz,7-H),

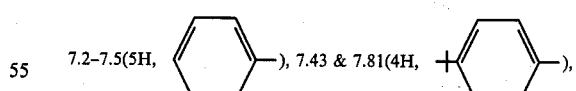

7.2–7.5(5H, ), 7.43 & 7.81(4H, ), 8.43(1H,d,J=8 Hz,—CH—NH—), 8.80(1H,d,J=8 Hz,—CONH—).

EXAMPLE 26

In dichloromethane (50 ml) was dissolved 7$\beta$-(D-5-phthalimido-5-carboxyvaleramido)-3-hydroxymethyl-3-cephem-4-carboxylic acid ditriethylamine salt (7.05 g), followed by addition of O-carboxymandelic anhydride (2.38 g). The mixture was stirred at room temperature for 1 hour, after which time it was treated as in Example 23. The procedure provided 7$\beta$-(D-5- phthalimido-5-carboxyvaleramido)-3-mandelyloxymethyl-3-cephem-4-carboxylic acid (6.25 g).

IR(KBr): 1773, 1715, 1647(shoulder) cm$^{-1}$.

NMR($\delta$ in d$_6$-DMSO): 1.54 & 2.22(6H,—(CH$_2$)$_3$—), 3.27 & 3.49(2H,ABq,J=18 Hz,2-CH$_2$),

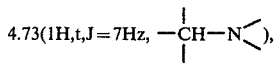
4.73(1H,t,J=7Hz, —CH—N⟨ ), 4.74 & 5.03(2H,ABq,J=13 Hz,3-CH$_2$), 4.98(1H,d,J=5 Hz,6-H),

5.16(1H,s, —CH—), 5.61(1H,dd,J=5 & 8 Hz,7-H),

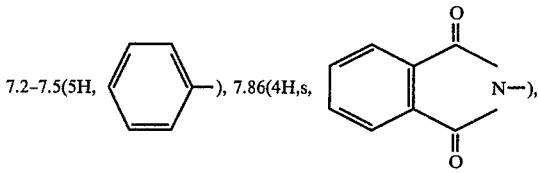
7.2-7.5(5H, —), 7.86(4H,s, N—), 8.77(1H,d,J=8 Hz,—CONH—).

EXAMPLE 27

In dichloromethane (75 ml) was suspended 7$\beta$-[D-5-phthalimido-5-carboxyvaleramido]-3-(2-carboxybenzoyloxy)methyl-3-cephem-4-carboxylic acid (6.51 g). Then, at a temperature not exceeding 10° C., triethylamine (4.20 ml) was added. To the solution thus obtained was added, N,N-dimethylaniline (10.0 ml) together with dimethyldichlorosilane (4.40 ml). The mixture was stirred at 20°-25° C. for 30 minutes. The mixture was then cooled to −30° C., followed by addition of phosphorus pentachloride (4.20 g). It was then reacted at −25°±2° C. for 30 minutes, after which time methanol (25 ml) was added dropwise at a temperature not exceeding −20° C. The mixture was reacted at −15°−−10° C. for 20 minutes and, after the addition of water (50 ml), was stirred vigorously for 5 minutes. The reaction mixture was separated and the aqueous layer was taken, washed with ethyl acetate and adjusted to pH 3.2 with 40% aqueous potassium carbonate solution. The resultant crystals were collected by filtration, washed with water, 50% aqueous methanol and acetone in the order mentioned and dried. The procedure provided 7$\beta$-amino-3-(2-carboxybenzoyloxy)methyl-3-cephem-4-carboxylic acid (3.43 g).

IR(KBr): 3170, 1798, 1730, 1700, 1615 cm$^{-1}$.

NMR($\delta$ in D$_2$O+NaOD): 3.55(2H,ABq,J=18 Hz), 4.6-5.6(4H,m),7.30-7.90(4H,m).

EXAMPLE 28

In dichloromethane (70 ml) was suspended 7$\beta$-[D-5-phthalimido-5-carboxyvaleramido]-3-(3-oxobutyryloxy)methyl-3-cephem-4-carboxylic acid (5.88 g). Then, at a temperature not exceeding 10° C., triethylamine (2.80 ml) was added, followed by the addition of N,N-dimethylaniline (10.0 ml) and dimethyldichlorosilane (3.13 ml). The mixture was stirred at 20°-25° C. for 30 minutes, after which phosphorus pentachloride (4.20 g) was added at −30° C. The mixture was reacted at −25°±2° C. for 30 minutes, after which time methanol (25 ml) was added dropwise at a temperature not exceeding −20° C. The reaction was further allowed to proceed at −15°−−10° C. for 20 minutes and, then, water (50 ml) was added at −15°−−10° C., followed by vigorous stirring for 5 minutes. The water layer was taken, washed with dichloromethane and adjusted to pH 3.5 with a 40% aqueous solution of potassium carbonate. The resultant crystals were recovered by filtration, washed with water, 50% aqueous methanol and acetone, and finally dried. The procedure provided 7$\beta$-amino-3-(3-oxobutyryloxy)methyl-3-cephem-4-carboxylic acid (2.84 g).

IR(KBr): 3200, 1800, 1745, 1720, 1622 cm$^{-1}$.

NMR($\delta$ in D$_2$O+NaOD): 2.27(3H,s), 3.48(2H,ABq,J=18 Hz), 4.6-5.6(4H,m).

EXAMPLE 29

In dimethylformamide (70 ml) was suspended desacetylcephalosporin C (13.7 g), followed by the addition of concentrated sulfuric acid (2.4 ml). To the resultant solution was added triethylamine (29 ml), together with N-carboethoxyphthalimide (8.5 g). The mixture was stirred at 30° C. for 50 minutes, followed by the addition of succinic anhydride (3.0 g). The mixture was stirred for 30 minutes, at the end of which time a further amount (0.6 g) of succinic anhydride was added. The mixture was further stirred for 1 hour and, then, poured in a cold saturated aqueous solution of sodium chloride (200 ml). The solution was made acidic with phosphoric acid and extracted three times with ethyl acetate. The extract was extracted back into a solution of sodium hydrogen carbonate (8 g) in water (150 ml). The water layer was adjusted to pH 1.7 with phosphoric acid and extracted with a mixture of tetrahydrofuran and dichloromethane (1:4). The extract was dried over magnesium sulfate, filtered and, with the addition of triethylamine (18 ml), concentrated to dryness. To the residue was added dichloromethane (200 ml) together with triethylamine (6 ml) and dimethylaniline (30 ml). Then, following the addition of dimethyldichlorosilane (21 ml), the mixture was stirred for 30 minutes, after which it was cooled to −30° C. and phosphorus pentachloride (20 g) was added. The mixture was stirred at −30° C. for 30 minutes and, following the addition of methanol (63 ml), it was further stirred for 30 minutes. Then, it was diluted with water (120 ml), brought to pH 3.0 and allowed to cool. The resultant crystals were recovered by filtration. The above procedure provided 7-amino-3-(3-carboxypropionyloxy)methyl-3-cephem-4-carboxylic acid (5.4 g).

IR(KBr): 1802, 1735, 1720(shoulder)cm$^{-1}$.

EXAMPLE 30

To 7$\beta$-[D-5-(p-t-butylbenzamido)-5-carboxyvaleramido]-3-mandelyloxymethyl-3-cephem-4-carboxylic acid (6.67 g) was added dichloromethane (60 ml) and, under cooling with ice, dimethylaniline (3.78 ml) and triethylamine (4.20 ml) was added. To the resultant solution was added dimethyldichlorosilane (3.87 g), followed by stirring at 8°-15° C. for 1 hour. Then, at −30° C., dimethylaniline (1.26 ml) and phosphorus pentachloride (4.17 g) were added. The mixture was stirred at −30°−−20° C. for 2 hours. Then, at −45° C., methanol (30 ml) was added dropwise over a period of 10 minutes. After the dropwise addition had been completed, the mixture was stirred at −10°−−5° C. for 40 minutes and, then, water (20 ml) was added dropwise over 5 minutes. Then, the mixture was adjusted to pH 3.3 with concentrated aqueous ammonia, whereupon a white slurry separated. After an hour of standing under ice-cooling, the precipitate was recovered by filtration, washed with water, methanol and ether in the order mentioned and dried under reduced pressure over phosphorus pentoxide.

The procedure provided 7β-amino-3-mandelyloxymethyl-3-cephem-4-carboxylic acid (2.31 g).

IR(KBr): 1800, 1740, 1621 cm$^{-1}$.

EXAMPLE 31

To 7β-[D-5(p-t-butylbenzamido)-5-carboxyvaleramido]-3-[2-carboxy-6 (or 3)-nitrobenzoyloxy]methyl-3-cephem-4-carboxylic acid (7.26 g) was added dichloromethane (60 ml) and, under cooling with ice, dimethylaniline (3.78 ml) and triethylamine (4.20 ml) were added. To the resultant solution was added dimethyldichlorosilane (3.87 g), followed by stirring at 7°−15° C. for 1 hour. The mixture was cooled to −30° C. and dimethylaniline (1.26 ml) and phosphorous pentachloride (4.17 g) were added. The mixture was stirred at −30°−−20° C. for 2 hours, after which time it was cooled to −45° C. and methanol (30 ml) was added dropwise over a period of 15 minutes. After the dropwise addition had been completed, the mixture was stirred at −10°−−8° C. for 40 minutes and, then, water (20 ml) was added dropwise over 10 minutes. The mixture was then adjusted to pH 3.4 with concentrated aqueous ammonia, whereupon a substantially white slurry separated. After 45 minutes' standing under ice-cooling, the precipitate was recovered by filtration and washed with water, methanol and ether in the order mentioned. It was then dried under reduced pressure over phosphorous pentoxide. The procedure provided 7β-amino-3-[2-carboxy-6 (or 3)-nitrobenzoyloxy]methyl-3-cephem-4-carboxylic acid (2.93 g).

IR(KBr): 1787, 1734, 1614, 1535, 1350 cm$^{-1}$.

EXAMPLE 32

In water (48 ml) was suspended 7β-amino-3-(2-carboxybenzoyloxy)methyl-3-cephem-4-carboxylic acid (7.33 g) and, at 0°−3° C., 2 N-sodium hydroxide (19.5 ml) was added in small installments, care being used not to allow the pH to exceed 8.5. Then, following the addition of sodium hydrogen carbonate (3.65 g), a solution of D-α-sulfophenylacetyl chloride (5.0 g) in ethyl acetate (8.8 ml) was added dropwise at 0°−5° C. over a period of 1 hour. After the dropwise addition had been completed, the reaction was carried out at 0°−5° C. for 20 minutes. The reaction mixture was adjusted to pH 5.5 and separated. The water layer was taken, degassed and, after confirming that the pH was within the range of 5.5 to 6.5, ethanol (800 ml) was added over a period of 1 hour. Thereafter, the mixture was stirred for 30 minutes, followed by cooling to a temperature not exceeding 5° C. The resultant crystals were recovered by filtration, washed with ethanol-water (10:1) and ethanol in the order mentioned and dried. The procedure provided 7β-(D-α-sulfophenylacetamido)-3-(2-carboxybenzoyloxy)-methyl-3-cephem-4-carboxylic acid trisodium salt (11.6 g).

IR(KBr): 3350, 1768, 1735, 1670, 1610 cm$^{-1}$.

NMR(δ in D$_2$O): 3.44(2H, ABq, J=18 Hz), 5.00(2H, ABq, J=13 Hz), 5.06(1H, d, J=5 Hz), 5.08(1H, s), 5.67(1H, d, J=5 Hz), 7.3−7.9(m, 9H).

EXAMPLE 33

In water (48 ml) was suspended 7β-amino-3-(3-oxobutyryloxy)methyl-3-cephem-4-carboxylic acid (6.09 g) and, at 0°−3° C., 2 N-sodium hydroxide (10.4 ml) was added in small installments, care being used not to allow the pH to exceed 8.5. Then, following the addition of sodium hydrogen carbonate (3.65 g), a solution of D-α-sulfophenylacetyl chloride (5.0 g) in ethyl acetate (8.8 ml) was added dropwise at 0°−5° C. over a period of 1 hour. After the dropwise addition had been completed, the reaction was carried out at 0°−5° C. for 20 minutes. Then, the reaction mixture was adjusted to pH 5.5 and separated. The water layer was taken, degassed and, after confirming that the pH was within the range of 5.5 to 6.5, ethanol (800 ml) was added to this aqueous solution (about 80 ml). Thereafter, the mixture was stirred for 30 minutes, at the end of which time it was cooled to a temperature not exceeding 5° C. The resultant crystals were recovered by filtration, washed with ethanol-water (10:1) and ethanol, and dried. The procedure provided 7β-(D-α-sulfophenylacetamido)-3-(3-oxobutyryloxy)methyl-3-cephem-4-carboxylic acid disodium salt (8.8 g).

IR(KBr): 3300, 1763, 1740, 1680, 1610, 1215, 1047 cm$^{-1}$.

NMR(δ in D$_2$O):

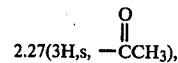

2.27(3H,s, —CCH$_3$), 3.29(2H, ABq, J=18 Hz, 2-CH$_2$), 4.84(2H, ABq, J=13 Hz, 3-CH$_2$), 5.00(1H, d, J=5 Hz, 6-H),

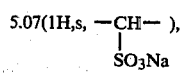

5.07(1H,s, —CH— ),
          |
          SO$_3$Na 5.70(1H, d, J=5 Hz, 7-H), 7.25−7.80(5H, m).

EXAMPLE 34

In dimethylformamide (10 ml) was dissolved 7β-(D-α-sulfophenylacetamido)-3-hydroxymethyl-3-cephem-4-carboxylic acid disodium salt (940 mg) together with glutaric anhydride (580 mg) and triethylamine (404 mg). The mixture was stirred at room temperature for 2 hours, after which time the dimethylformamide was distilled off. To the residue was added a small amount of water and the aqueous solution was desalted with Amberlite IR-120(H), adjusted to pH 6.0 with 1 N-sodium hydroxide solution and lyophilized. The lyophilizate was re-dissolved in water and purified by column chromatography on Amberlite XAD-2. The procedure provided 7β-(D-α-sulfophenylacetamido)-3-(4-carboxybutyryloxy)methyl-3-cephem-4-carboxylic acid trisodium salt.

IR(KBr): 1760, 1675, 1620 cm$^{-1}$.

NMR(δ in D$_2$O): 1.65−2.60(6H, m), 3.41(2H, q, 2-CH$_2$), 4.83(2H, d, 3-CH$_2$),

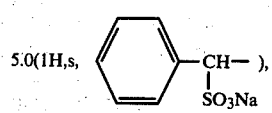

5.0(1H,s,         —CH— ),
                   |
                   SO$_3$Na 5.08(1H, d, 6-H), 5.75(1H, d, 7-H), 7.47(5H, m).

EXAMPLE 35

In dimethylformamide (3 ml) was dissolved 7β-(D-α-sulfophenylacetamido)-3-hydroxymethyl-3-cephem-4-carboxylic acid disodium salt (470 mg) together with succinic anhydride (250 mg) and triethylamine (200 mg). The mixture was stirred at room temperature for 2 hours. It was then diluted with a small amount of water and the dimethylformamide was distilled off under reduced pressure. The residue was dissolved by the addition of water and purified by column-chromatography on Amberlite XAD-2. The procedure provided 7β-(D-α-sulfophenylacetamido)-3-(3-carboxypropionyloxy)-methyl-3-cephem-4-carboxylic acid trisodium salt.

IR(KBr): 1765, 1685, 1600 cm$^{-1}$.

NMR(δ in D$_2$O): 2.62(4H, s, —CO(CH$_2$)$_2$CO—), 3.38(2H, q, 2-CH$_2$), 4.95(2H, 3-CH$_2$),

5.10(1H,s, 5.21(1H, d, 6-H), 5.91(1H, d, 7-H),

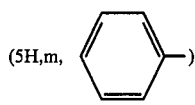

(5H,m,

EXAMPLE 36

In chloroform (5 ml) was dissolved 7β-(D-α-sulfophenylacetamido)-3-hydroxymethyl-3-cephem-4-carboxylic acid ditriethylamine salt (480 mg), followed by the addition of diketene (300 mg). The mixture was stirred at room temperature for 2 hours, after which the solvent was distilled off. The residue was diluted with water and desalted with Amberlite IR-120(H). The desalted solution was adjusted to pH 5.7 with 1 N-sodium hydroxide solution and lyophilized. Yield 400 mg. The lyophilizate was purified by column chromatography on Amberlite XAD-2. The procedure provided 7β-(D-α-sulfophenylacetamido)-3-(3-oxobutyryloxy)methyl-3-cephem-4-carboxylic acid disodium salt.

In IR and NMR spectra, this product was found in good agreement with the product obtained in Example 33.

EXAMPLE 37

In dichloromethane (80 ml) was suspended 7β-amino-3-(3-oxobutyryloxy)methyl-3-cephem-4-carboxylic acid (15.7 g). At −10° C., triethylamine (10.1 g) was added. To the resultant solution was added a solution of 4-chloro-3-oxobutyryl chloride (1.41 mMol/g) (44.9 g) dropwise at −20°−−15° C. over a period of 20 minutes. After the dropwise addition had been completed, the reaction was carried out at a temperature not exceeding −5° C. for 1 hour. After the reaction, the dichloromethane was distilled off and the residue was dissolved by the addition of tetrahydrofuran (50 ml), ethyl acetate (100 ml) and 10% aqueous phosphoric acid. The resultant solution was separated and the organic layer was taken. The water layer was extracted with a solvent mixture of ethyl acetate-tetrahydrofuran (5:1). The extracts were pooled, washed with a saturated aqueous solution of sodium chloride, dried over magnesium sulfate and filtered. The solvent was distilled off and the residue was treated with ethyl acetate-ether. The resulted powder was recovered by filtration, washed with ether and dried. The procedure provided 7β-(4-chloro-3-oxobutylamido)-3-(3-oxobutyryloxy)methyl-3-cephem-4-carboxylic acid (20.4 g).

IR(KBr): 3325, 1782, 1740, 1732, 1715, 1685, 1650 cm$^{-1}$.

NMR(δ in d$_6$-DMSO): 2.14(3H, s), 3.55(4H, s), 3.54(2H, br), 4.44(2H, s), 4.90(2H, ABq, J=13 Hz), 5.05(1H, d, J=5 Hz), 5.54(1H, q, J=5 & 8 Hz), 8.96(1H, d, J=8 Hz).

The dichloromethane solution of 4-chloro-3-oxobutyryl chloride used in this reaction was prepared by dissolving diketene (84.0 g) in dichloromethane (420 ml) and introducing chlorine gas (78.1 g) at −30°−−35° C. for one hour.

EXAMPLE 38

While a solution of diketene (0.91 g) in dichloromethane (2 ml) was stirred at −40°−−30° C., bromine (1.82 g) was added dropwise. Separately, 7β-amino-3-(3-oxobutyryloxy)methyl-3-cephem-4-carboxylic acid (2.6 g) and triethylamine (1.7 g) were dissolved in dichloromethane (20 ml) and cooled to −40° C. This solution was added to the above reaction mixture. After stirring for 20 minutes, the mixture was further stirred under cooling with ice. Following the addition of water (7 ml), phosphoric acid and ethyl acetate, the mixture was stirred vigorously and the organic layer was washed with an aqueous solution of sodium chloride, dried and decolorized with activated carbon. Then, the solvent was distilled off and ether was added. The procedure provided 7β-(4-bromo-3-oxobutylamido)-3-(3-oxobutyryloxy)methyl-3-cephem-4-carboxylic acid (2.4 g).

IR(KBr): 1790, 1730, 1645, 1545 cm$^{-1}$.

NMR(δ in d$_6$-DMSO): 2.17(3H, s, COCH$_3$), 3.60(2H, s, —COCH$_2$CO—), 3.3–3.8(2H, broad, 2-CH$_2$), 4.36(2H, s, BrCH$_2$CO—), 4.76 & 5.06(2H, ABq, J=12 Hz, 3-CH$_2$), 5.07(1H, d, J=4.5 Hz, 6-H), 5.68(1H, dd, J=4.5 & 8 Hz, 7-H), 9.04(1H, d, J=8 Hz, —CONH—)

EXAMPLE 39

A solution of diketene (0.20 ml) in dichloromethane (1 ml) was stirred at −30° C., a 1.5 M solution of chlorine in carbon tetrachloride (2.0 g) was added dropwise over a period of 10 minutes. The mixture was further stirred at −25°−−35° C. for 30 minutes. Separately, 7β-amino-3-[2-carboxy-6(or 3)-nitrobenzoyloxy]methyl-3-cephem-4-carboxylic acid (0.90 g) and triethylamine (0.84 ml) were dissolved in dichloromethane (5 ml) and cooled to −5°−−10° C. To this solution was added the above reaction mixture dropwise at −20°−−30° C. over a period of 15 minutes. The mixture was then stirred at the same temperature for 45 minutes. Then, the reaction mixture was distilled under reduced pressure and the residue was stirred vigorously with ethyl acetate (25 ml), tetrahydrofuran (5 ml) and 10% aqueous phosphoric acid (20 ml). The organic layer was washed with a saturated aqueous solution of sodium chloride (15 ml), dried over sodium sulfate and concentrated under reduced pressure. Then, upon addition of ether, there was obtained a powder. This powder was recovered by filtration, washed with ether (10 ml) and dried under reduced pressure over phosphorus pentoxide. The procedure provided 7β-(4-chloro-3- oxobutylamido)-3-[2-carboxy-6(or 3)-nitrobenzoyloxy]-methyl-3-cephem-4-carboxylic acid (0.70 g).

NMR(δ in d$_6$-DMSO): 3.4–3.8(2H, 2-CH$_2$), 3.54(2H, s, —COCH$_2$CO—), 4.52(2H, s, ClCH$_2$—), 4.94 & 5.22(2H, ABq, J=13 Hz, 3-CH$_2$), 5.04(1H, d, J=5 Hz, 6-H), 5.68(1H, dd, J=5 & 8 Hz, 7-H),

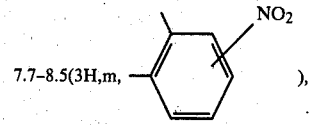

9.04(1H, d, J=8 Hz, —CONH—).

EXAMPLE 40

In acetone (10 ml) was dissolved 7β-(4-chloro-3-oxobutylamido)-3-(3-oxobutyryloxy)methyl-3-cephem-4-carboxylic acid (4.33 g) and, under cooling with ice, water (10 ml) and thiourea (0.84 g) were added. Then, sodium hydrogen carbonate (0.84 g) and water (10 ml) were further added. The mixture was reacted at room temperature for 5 hours, after which time it was cooled with ice. The resultant crystals were collected by filtration, washed with water, acetone and ether and dried. The procedure provided 7β-[2-(2-imino-4-thiazolin-4-yl)acetamido]-3-(3-oxobutyryloxy)methyl-3-cephem-4-carboxylic acid (4.22 g).

IR(KBr): 1775, 1740, 1710, 1661 cm$^{-1}$.

NMR(δ in d$_6$-DMSO):

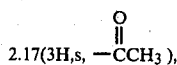

3.38(2H, s, —CH$_2$CONH—), 3.51(2H, 2-CH$_2$),

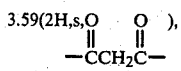

4.77 & 5.06(2H, ABq, J=13 Hz, 3-CH$_2$), 5.05 (1H, d, J=5 Hz, 6-H), 5.69(1H, dd, J=5 & 9 Hz, 7-H), 6.23 (1H, s, thiazoline-H), 8.82(1H, d, J=9 Hz, —CONH—).

EXAMPLE 41

In dimethylformamide (3.5 ml) was dissolved 7β-[2-(2-imino-4-thiazolin-4-yl)acetamido]-3-hydroxymethyl-3-cephem-4-carboxylic acid sodium salt (1.37 g), followed by the addition of O-carboxymandelic anhydride (0.90 g). The mixture was stirred at room temperature for one hour, after which time most of the dimethylformamide was distilled off under reduced pressure. To the residue was added ethyl acetate (50 ml), followed by vigorous stirring. The resultant powder was recovered by filtration, washed with ethyl acetate (20 ml), dichloromethane (20 ml) and ether (20 ml) in the order mentioned. The procedure provided 7β-[2-(2-imino-4-thiazolin-4-yl)acetamido]-3-mandelyloxymethyl-3-cephem-4-carboxylic acid (1.60 g).

IR(KBr): 1780, 1743, 1665, 1643, 1537 cm$^{-1}$.

NMR(δ in d$_6$-DMSO+D$_2$O): 3.33 & 3.65(2H, ABq, J=18 Hz, 2—CH$_2$), 3.37(2H, s, —CH$_2$CO—), 4.8–5.3(2H, 3-CH$_2$), 4.97(1H, d, J=5 Hz, 6-H),

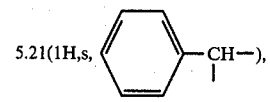

5.64(1H, d, J=5 Hz, 7-H), 6.25(1H, s, thiazolin-H),

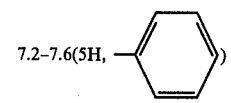

EXAMPLE 42

In N,N-dimethylformamide (20 ml) was dissolved 7β-(2-thienylacetamido)-3-hydroxymethyl-3-cephem-4-carboxylic acid sodium salt (3.86 g) and, at −5° C., triethylamine (1.40 ml) and diketene (1.50 ml) were added. The reaction was carried out at −5°-0° C. for 1 hour, after which time the reaction mixture was poured in ice-water (200 ml). The mixture was adjusted to pH 2.0 with 4 N-hydrochloric acid and extracted with ethyl acetate. The ethyl acetate layer was rinsed with water, diluted with water, brought to pH 7.0 with 5% aqueous sodium hydrogen carbonate solution and separated. The water layer was taken, concentrated and subjected to column-chromatography on Amberlite XAD-2, elution being carried out with water-methanol. The eluate was lyophilized. The above procedure provided 7β-(2-thienylacetamido)-3-(3-oxobutyryloxy)methyl-3-cephem-4-carboxylic acid sodium salt (4.48 g).

IR(KBr): 3300, 1765, 1745, 1670, 1613 cm$^{-1}$.

NMR(δ in D$_2$O): 2.31(3H, s), 3.47(2H, ABq, J=18 Hz), 3.85(2H, s), 4.88(2H, ABq, J=13 Hz), 5.08(1H, d, J=5 Hz), 5.60 (1H, d, J=5 Hz), 6.9–7.5(3H, m).

EXAMPLE 43

In dichloromethane (50 ml) was dissolved 7β-phenylacetamido-3-hydroxymethyl-3-cephem-4-carboxylic acid triethylamine salt (4.5 g), followed by the addition of succinic anhydride (1.5 g). The mixture was stirred at room temperature for 5 hours, after which time the solvent was distilled off under reduced pressure. Then, following the addition of water and ethyl acetate, the residue was adjusted to pH 2.0 with phosphoric acid. The ethyl acetate layer was dried and concentrated. The resultant crystals were collected by filtration (2.9 g). The mother fluid was further concentrated and, after the addition of ether, the concentrate was allowed to stand, whereupon crystals (1.6 g) were obtained. These crystals were recrystallized from ethyl acetate.

The procedure provided 7β-phenylacetamido-3-(3-carboxypropionyloxy)methyl-3-cephem-4-carboxylic acid, melting point: 86°–89° C.

IR(KBr): 1800, 1735, 1692, 1660 cm$^{-1}$.

NMR(δ in d$_6$-DMSO): 2.48(4H, —(CH$_2$)$_2$—), 3.51(4H, 2—CH$_2$, —CH$_2$CO—), 4.69 & 5.02(2H, ABq, J=13 Hz), 5.00(1H, d, J=5 Hz, 6-H), 5.63(1H, dd, J=5 & 9 Hz, 7-H), 7.23(5H, 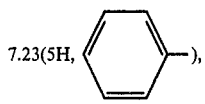), 9.02 (1H, d, J=9 Hz, —CONH—).

EXAMPLE 44

The reaction procedure of Example 43 was repeated except that phthalic anhydride (2.2 g) was used in place of succinic anhydride. This procedure provided 7β-phenylacetamido-3-(2-carboxybenzoyloxy)methyl-3-cephem-4-carboxylic acid. Melting point: 128°–129° C.(ethyl acetate-ether).

IR(KBr): 1788, 1731, 1695, 1662 cm$^{-1}$.

NMR(δ in d$_6$-DMSO): 3.53(2H, s, —CH$_2$CO—), 3.61(2H, 2-CH$_2$), 4.90 & 5.27(2H, ABq, J=13 Hz, 3—CH$_2$), 5.08(1H, d, J=5 Hz, 6-H), 5.68(1H, dd, J=5 & 8 Hz, 7-H),

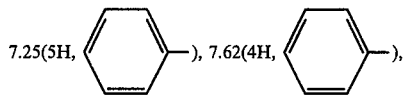

9.07(1H, d, J=8 Hz, —CONH—).

EXAMPLE 45

Dichloromethane (20 ml) was added to a mixture of 7β-amino-3-(3-oxobutyryloxy)methyl-3-cephem-4-carboxylic acid (3.14 g) and dimethylacetamide (1.8 g). Then, under ice-cooling and stirring, phenoxyacetyl chloride (1.8 g) was added. The mixture was stirred for 1 hour, after which the insolubles were filtered off and the filtrate washed with an aqueous solution of sodium chloride. The organic layer was extracted with aqueous sodium hydrogen carbonate solution. The water layer was made acidic with phosphoric acid and extracted with ethyl acetate. The extract was washed with aqueous sodium chloride solution, dried and distilled to remove the solvent. To the residue was added ether and the resultant powder was recovered by filtration and washed with ether.

The procedure provided 7β-phenoxyacetamido-3-(3-oxobutyryloxy)methyl-3-cephem-4-carboxylic acid.

IR(KBr): 1788, 1722 cm$^{-1}$.

NMR(δ in d$_6$-DMSO):

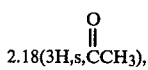

3.60(2H,2—CH$_2$),

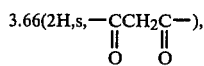

4.67(2H,s,—OCH$_2$—), 4.99(2H,3—CH$_2$), 5.18(1H, d, J=5 Hz, 6-H), 5.78(1H, dd, J=5 & 8 Hz, 7-H), 6.8–7.7(5H, m), 9.07(1H, d, J=8 Hz).

EXAMPLE 46

In dichloromethane (5 ml) was suspended 7β-amino-3-(3-oxobutyryloxy)methyl-3-cephem-4-carboxylic acid (314 mg) and, at −10° C., triethylamine (0.28 ml) was added. To the resultant solution was added diketene (0.2 ml), and the reaction was carried out at a temperature not exceeding 0° C. for 2 hours. After this reaction, the dichloromethane was distilled off and the residue was dissolved in water-ethyl acetate, adjusted to pH 2.0 with 4N-hydrochloric acid and separated. The ethyl acetate layer was taken, diluted with water, adjusted to pH 7.0 with 5% aqueous sodium hydrogen carbonate, and separated. The water layer was taken, concentrated and subjected to column-chromatography on Amberlite XAD-2, elution being carried out with water-methanol. The eluate was lyophilized. The above procedure provided 7β-(3-oxobutylamido)-3-(3-oxobutyryloxy)methyl-3-cephem-4-carboxylic acid sodium salt (375 mg).

IR(KBr): 3320, 1770, 1745, 1660, 1610 cm$^{-1}$.

NMR(δ in D$_2$O): 2.27(6H,s), 3.55(2H, ABq,J=18 Hz), 4.93(2H, ABq,J=13 Hz), 5.15 (1H,d,J=5 Hz), 5.70(1H,d,J=5 Hz).

EXAMPLE 47

In acetonitrile (5 ml) was dissolved 7β-(4-bromo-3-oxobutylamido)-3-(3-oxobutyryloxy)methyl-3-cephem-4-carboxylic acid (2.4 g), followed by the addition of thiocarbamic acid O-methyl ester (0.6 g). The mixture was stirred at room temperature overnight and the resultant crystals were recovered by filtration. The procedure provided 7β-[2-(2-oxo-4-thiazolin-4-yl)acetamido]-3-(3-oxobutyryloxy)methyl-3-cephem-4-carboxylic acid.

IR(KBr): 1780, 1722, 1675, 1629 cm$^{-1}$.

NMR(δ in d$_6$-DMSO): 2.17(3H,s,—COCH$_3$), 3.32(2H,s,—CH$_2$—CONH), 3.41 & 3.64(2H,ABq,J=18 Hz, 2-H), 3.58(2H,s,—COCH$_2$CO—), 4.75 & 5.06(2H,ABq,J=13 Hz), 5.06(1H,d,J=4.5 Hz, 6-H), 5.68(1H,dd,J=4.5 & 8 Hz, 7-H), 5.99(1H,s,thiazolin-H), 8.94(1H,d,J=8 Hz, —CONH—), 11.06(1H,thiazolin-NH)

EXAMPLE 48

In dichloromethane (7 ml) was suspended 7β-amino-3-(3-carboxypropionyloxy)methyl-3-cephem-4-carboxylic acid (660 mg), followed by the addition of N,N-dimethylacetamide (0.7 ml). Then, under ice-cooling and stirring, a solution of (1H-tetrazol-1-yl)acetyl chloride (294 mg) in dichloromethane (2 ml) was added. The mixture was stirred at room temperature for 1 hour, after which time it was poured in an aqueous solution of sodium hydrogen carbonate and separated. The water layer was taken, washed with dichloromethane, made acidic with phosphoric acid and extracted with ethyl acetate. The extract was re-extracted with aqueous sodium hydrogen carbonate solution to bring the desired compound into the aqueous phase. This aqueous solution was purified by column-chromatography on Sephadex LH-20. The fractions containing the dominant product were pooled and lyophilized. The procedure provided 7β-[2-(1H-tetrazol-1-yl)acetamido]-3-(3-carboxypropionyloxy)methyl-3-cephem-4-carboxylic acid disodium salt.

IR(KBr): 1765, 1620 cm$^{-1}$.

NMR(δ in D$_2$O): 2.60(4H,m,—(CH$_2$)$_2$—), 3.44 & 3.74(2H,ABq,J=17 Hz, 2-CH$_2$), 5.20(1H,d,J=5 Hz,6-H), 5.59(2H,s,NCH$_2$CO—), 5.76(1H,d,J=5 Hz, 7-H), 9.33(1H,s,tetrazol-H)

EXAMPLE 49

In dichloromethane (10 ml) was suspended 7β-amino-3-(3-oxobutyryloxy)methyl-3-cephem-4-carboxylic acid (942 mg), followed by the addition of N,N-dimethylacetamide (1 ml). Then, under ice-cooling and stirring, a solution of (1H-tetrazol-1-yl)acetyl chloride (441 mg) in dichloromethane (3 ml) was added. The mixture was further stirred at room temperature for 30 minutes, after which it was poured in an aqueous solution of sodium hydrogen carbonate. The water layer, i.e. aqueous extract, was purified by column-chromatography on Sephadex LH-20. The fractions rich in the desired product were pooled, concentrated, made acidic with phosphoric acid and extracted with ethyl acetate. The extract was dried, concentrated and treated with ether. The procedure provided 7β-[2-(1H-tetrazol-1-yl)acetamido]-3-(3-oxobutyryloxy)methyl-3-cephem-4-carboxylic acid.

IR(KBr): 1782, 1707 cm$^{-1}$.

NMR(δ in d$_6$-DMSO): 2.17(3H,s,—CH$_3$), 3.55(2H,broad, 2—CH$_2$),

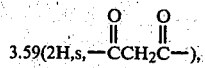

4.78 & 5.08(2H,ABq,J=13 Hz, 3-CH$_2$), 5.09(1H,d,J=5 Hz, 6-H), 5.34(2H,s,NCH$_2$CO—), 5.71(1H,dd,J=5 & 8 Hz,7-H), 9.28(1H,s,tetrazol-H), 9.46(1H,d,J=8 Hz,—CONH—).

EXAMPLE 50

In dry tetrahydrofuran (30 ml) was dissolved D-α-t-butoxycarbonylamino-α-(p-hydroxyphenyl)acetic acid (2.68 g), followed by the addition of 2,6-lutidine (1.08 g). While cooling at −10° C. and stirring, ethyl chloroformate (1.08 g) was gently added and the mixture was stirred at −10° C. for 20 minutes. An ice-cooled mixed solution of 7β-amino-3-(3-oxobutyryloxy)methyl-3-cephem-4-carboxylic acid (3.14 g) and sodium hydrogen carbonate (1.0 g) in water (30 ml) was added in a single dose to the above mixture. The entire mixture was stirred at −3° C. for 10 minutes and, then, under cooling with ice-water, for 2 hours. Following the addition of water (60 ml), the mixture was washed with ethyl acetate (50 ml) and, under stirring in the presence of ethyl acetate (100 ml), 50% phosphoric acid was gently added so as to bring the pH to 3.0. The ethyl acetate layer was taken, rinsed with water (100 ml), dried over anhydrous sodium sulfate and treated with a 2N-solution of sodium 2-ethylhexanoate in isopropyl alcohol (6 ml). The resultant precipitate was taken by decantation, loosened with ethyl acetate, recovered by filtration and dried under reduced pressure over phosphorus pentoxide. The brown powder thus obtained was purified by column-chromatography on Amberlite XAD-2. The procedure provided 7β-[D-α-t-butoxycarbonylamino-α-(p-hydroxyphenyl)acetamido]-3-(3-oxobutyryloxy)methyl-3-cephem-4-carboxylic acid sodium salt.

IR(KBr): 3400, 1770, 1680, 1610 cm$^{-1}$.

NMR(δ in D$_2$O): 1.45(9H,s), 2.30(3H,s), 3.43(2H,broad), 5.65(1H,d,J=5 Hz,7-H), 6.76–7.40(4H,m).

EXAMPLE 51

In water (0.3 ml) was dissolved 7β-(D-α-sulfophenylacetamido)-3-(3-oxobutyryloxy)methyl-3-cephem-4-carboxylic acid disodium salt (278 mg), together with pyridine (60 mg) and KSCN (1.2 g). The mixture was heated at 60° C. for 1 hour, after which it was subjected to column-chromatography on Amberlite XAD-2, elution being carried out with water. The fractions rich in the desired product were pooled, lyophilized and recrystallized from methanol. The procedure provided 7-(D-α-sulfophenylacetamido)-3-cephem-3-pyridinium-methyl-4-carboxylate sodium salt.

IR(KBr): 1760, 1665, 1610 cm$^{-1}$.

NMR(δ in D$_2$O): 2.97, 3.35(2H,ABq,J=18 Hz, 2-CH$_2$), 5.27, 5.40(2H,3-CH$_2$), 5.07(1H,d,J=5.2 Hz,6-H), 5.71(1H,d,βJ=5.2 Hz,7-H),

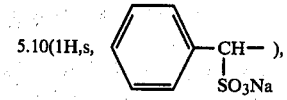

7.47(5H,m),

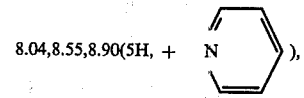

EXAMPLE 52

The reaction procedure of Example 51 was repeated using isonicotinamide (90 mg) in place of pyridine and the reaction product was treated in the same manner as Example 51. The procedure provided 7-(D-α-sulfophenylacetamido)-3-cephem-3-(4-carbamoylpyridinium)methyl-4-carboxylate sodium salt. It was purified by recrystallization from ethanol-water. Melting point: 175° C. (decomp.).

IR(KBr): 1765, 1692, 1645, 1615, 1029 cm$^{-1}$.

NMR(δ in D$_2$O): 2.99, 3.56(2H,ABq,J=18 Hz, 2-CH$_2$), 5.40, 5.51(2H,3-CH$_2$), 5.13(1H,d,J=4.8 Hz, 6-H); 5.73(1H,d,J=4.8 Hz,7-H),

7.40(5H,m), 8.31, 9.07(4H).

EXAMPLE 53

In 50% aqueous acetone (8 ml) was dissolved 7β-(2-thienylacetamido)-3-mandelyloxymethyl-3-cephem-4-carboxylic acid (0.49 g) together with acetylacetone (0.50 g) and sodium hydrogen carbonate (0.17 g), and the solution was stirred at 60° C. for 1 hour. The reaction mixture was brought to room temperature and most of the acetone was distilled off under reduced pressure. To the residue was added 5% aqueous phosphoric acid solution (10 ml), together with ethyl acetate (20 ml). The ethyl acetate layer was washed with a saturated aqueous solution of sodium chloride (20 ml), dried over magnesium sulfate and concentrated under reduced pressure. Then, upon addition of ether, there was obtained a powder. This powder was suspended in water (3 ml) and dissolved by the addition of sodium hydrogen carbonate. The solution was subjected to column-chromatography on Sephadex LH-20, elution being carried out with water. The desired fractions were pooled and lyophilized. The procedure provided 7β-(2-thienylacetamido)-3-(2-acetyl-3-oxo)butyl-3- cephem-4-carboxylic acid sodium salt (0.28 g). This product was dissolved in water (10 ml), followed by the addition of 10% aqueous phosphoric acid (2 ml) and ethyl acetate (20 ml). The ethyl acetate layer was rinsed with water, dried over magnesium sulfate and concentrated under reduced pressure. Then, upon addition of ether, there was obtained a powder. This powder was recovered by filtration, washed with ether and dried under reduced pressure over phosphorus pentoxide. The procedure provided 7β-(2-thienylacetamido)-3-(2-acetyl-3-oxo)butyl-3-cephem-4-carboxylic acid (0.23 g).

IR(KBr): 1765, 1718 cm$^{-1}$.

NMR(δ in d$_6$-DMSO): 2.13 & 2.18(6H,s,(COCH$_3$)$_2$), 2.6–3.1(2H, m, 3-CH$_2$), 3.31 & 3.56(2H, ABq, 2-CH$_2$), 3.75(2H,s,—CH$_2$CO—), 4.14(1H,—CH—), 5.01(1H,d,J=5 Hz,6-H), 5.58(1H,dd,J=5 & 8 Hz,7-H),

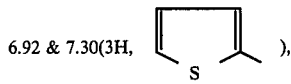
6.92 & 7.30(3H, 9.04(1H,d,J=8 Hz,—CONH—).

EXAMPLE 54

In 50% aqueous acetone (40 ml) was dissolved 7β-(2-thienylacetamido)-3-[2-carboxy-6(or 3)-nitrobenzoyloxy]methyl-3-cephem-4-carboxylic acid (2.65 g) together with acetylacetone (2.42 g) and sodium hydrogen carbonate (1.22 g). The mixture was stirred at 60° C. for 1 hour, after which time it was treated by a procedure similar to that described in Example 53. The procedure provided 7β-(2-thienylacetamido)-3-(2-acetyl-3-oxo)butyl-3-cephem-4-carboxylic acid (1.26 g). In IR and NMR spectra, this product was in good agreement with the product according to Example 53.

EXAMPLE 55

In 50% aqueous acetone (8 ml) was dissolved 7β-[D-5-(p-t-butylbenzamido)-5-carboxyvaleramido]-3-[2-carboxy-6 (or 3)-nitrobenzyloxy]methyl-3-cephem-4-carboxylic acid (0.73 g) together with acetylacetone (0.50 g) and sodium hydrogen carbonate (0.34 g). The mixture was stirred at 60° C. for 1 hour, after which it was treated by a procedure similar to that described in Example 53.

The procedure provided 7β-[D-5-(p-t-butylbenzamido)-5-carboxyvaleramido]-3-(2-acetyl-3-oxo)butyl-3-cephem-4-carboxylic acid (0.29 g).

IR(KBr): 1767, 1721, 1655, 1635 cm$^{-1}$.

NMR(δ in d$_6$-DMSO): 1.30(9H,s,—C(CH$_3$)$_3$), 1.76 & 2.25(6H,—(CH$_2$)$_3$—), 2.6–3.1(2H,m,3-CH$_2$), 3.2–3.6(2H,2-CH$_2$), 4.13(1H,—CH(COCH$_3$)$_2$), 4.37(1H,—CH—), 4.99(1H,d,J=5 Hz,6-H), 5.57(1H,dd,J=5 & 8 Hz,7-H),

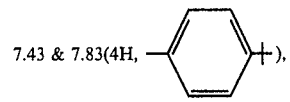
7.43 & 7.83(4H, 8.40(1H, d, J=8 Hz, —CH—NH—), 8.77(1H, d, J=8 Hz, —CONH—).

EXAMPLE 56

In 50% aqueous acetone (8 ml) was dissolved 7β-[D-5-(p-t-butylbenzamido)-5-carboxyvaleramido]-3-mandelyloxymethyl-3-cephem-4-carboxylic acid (0.67 g), together with acetylacetone (0.50 g) and sodium hydrogen carbonate (0.25 g). The mixture was stirred at 60° C. for 1.5 hours, after which it was treated by a procedure similar to that described in Example 53. The procedure provided 7β-[D-5-(p-t-butylbenzamido)-5-carboxyvaleramido]-3-(2-acetyl-3-oxo)butyl-3-cephem-4-carboxylic acid (0.33 g). In IR and NMR spectra, this product was in agreement with the product obtained in Example 55.

EXAMPLE 57

In 50% aqueous acetone (14 ml) was dissolved 7β-[D-5-(p-t-butylbenzamido)-5-carboxyvaleramido]-3-[2-carboxy-6 (or 3)-nitrobenzoyloxy)methyl-3-cephem-4-carboxylic acid (0.73 g), pyrrole (0.20 g) and sodium hydrogen carbonate (0.25 g). The mixture was stirred at 60° C. for 1 hour, after which it was brought down to room temperature and most of the acetone was distilled off under reduced pressure. Then, 5% aqueous phosphoric acid solution (15 ml) and ethyl acetate (30 ml) were added. The ethyl acetate layer was washed with a saturated aqueous solution of sodium chloride (20 ml), dried (over magnesium sulfate) and concentrated under reduced pressure. Then, upon addition of ether, there was obtained a powder. This powder was suspended in water (3 ml) and dissolved by the addition of sodium hydrogen carbonate (0.17 g). The solution was subjected to column-chromatography on Sephadex LH-20(250 ml), elution being carried out with water. The fractions containing the desired product were pooled and lyophilized. The above procedure provided 7β-[D-5-(p-t-butylbenzamido)-5-carboxyvaleramido]-3-(2-pyrrolyl)methyl-3-cephem-4-carboxylic acid disodium salt (0.29 g).

IR(KBr): 1760, 1600 cm$^{-1}$.

NMR(δ in D$_2$O): 1.23(9H,s,—C(CH$_3$)$_3$), 1.86 & 2.42(6H,—(CH$_2$)$_3$—), 2.86 & 3.25(2H,ABq,J=18 Hz, 2-CH$_2$), 3.42 & 3.73(2H,ABq,J=15 Hz,3-CH$_2$),

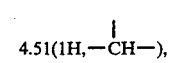
4.51(1H,—CH—), 4.96(1H, d, J=5 Hz, 6-H), 5.61(1H,d,J=5 Hz,7-H), 5.93(1H, pyrrole-3-H), 6.07(1H, pyrrole-4-H), 6.77(1H, pyrrole-5-H),

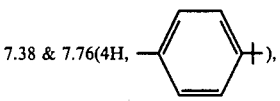
7.38 & 7.76(4H, 7.80(1H, pyrrole-1-H).

EXAMPLE 58

In 50% aqueous acetone (14 ml) was dissolved 7β-[D-5-(p-t-butylbenzamido)-5-carboxyvaleramido]-3-[2-carboxy-6 (or 3)-nitrobenzoyloxy]methyl-3-cephem-4-carboxylic acid (0.73 g), together with N-methylpyrrole (0.24 g) and sodium hydrogen carbonate (0.25 g). The mixture was stirred at 60° C. for 1 hour. After the reaction had been completed, the mixture was treated in the same manner as Example 57. The procedure provided 7β-[D-5-(p-t-butylbenzamido)-5-carboxyvaleramido]-3-(N-methylpyrrol-2-yl)-methyl-3-cephem-4-carboxylic acid disodium salt (0.21 g).

IR(KBr): 1757, 1597 cm$^{-1}$.

NMR(δ in D$_2$O): 1.21(9H,s,—C(CH$_3$)$_3$), 1.87 & 2.45(6H,—(CH$_2$)$_3$—), 2.79 & 3.07(2H,ABq,J=18 Hz,2-CH$_2$), 3.46(3H,s,N-CH$_3$), 3.51 & 3.87(2H,ABq,J=15 Hz,3-CH$_2$), 4.51(1H,—CH—), 4.91(1H,d,J=5 Hz,6-H), 5.58(1H,d,J=5 Hz,7-H), 5.86(1H, pyrrole-3-H), 5.99(1H,pyrrole-4-H), 6.61(1H,pyrrole-5-H),

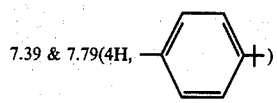
7.39 & 7.79(4H,

EXAMPLE 59

In 50% aqueous acetone (12 ml) was dissolved 7β-(D-5-phthalimido-5-carboxyvaleramido)-3-mandelyloxymethyl-3-cephem-4-carboxylic acid (0.64 g), together with indole (0.35 g) and sodium hydrogen carbonate (0.17 g). The mixture was stirred at 60° C. for 1 hour. Following the completion of the reaction, the mixture was treated by a procedure similar to that described in Example 57. The procedure provided 7β-(D-5-phthalimido-5-carboxyvaleramido)-3-(3-indolyl)methyl-3-cephem-4-carboxylic acid disodium salt (0.24 g).

IR(KBr): 1758, 1702, 1600 cm$^{-1}$.

NMR(δ in D$_2$O): 1.68 & 2.26(6H,—(CH$_2$)$_3$—), 2.45 & 2.82(2H,Abq,J=18 Hz,2-CH$_2$), 3.61 & 3.86(2H,ABq,J=15 Hz,3-CH$_2$), 4.6–4.9(2H,—CH— & 6-H), 5.46(1H,d,J=5 Hz,7-H),

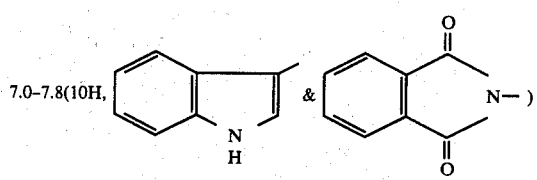
7.0–7.8(10H,

EXAMPLE 60

In 50% aqueous acetone (14 ml) was dissolved 7β-(D-5-phthalimido-5-carboxyvaleramido)-3-[2-carboxy-6 (or 3)-nitrobenzoyloxy]methyl-3-cephem-4-carboxylic acid (0.70 g), together with indole (0.35 g) and sodium hydrogen carbonate (0.25 g). The mixture was stirred at 60° C. for 45 minutes and, after the reaction had been completed, it was treated by a procedure similar to that described in Example 57. The procedure provided 7β-(D-5-phthalimido-5-carboxyvaleramido)-3-(3-indolyl)methyl-3-cephem-4-carboxylic acid disodium salt (0.22 g). In IR spectrum, this product was found to agree with the product obtained in Example 59.

EXAMPLE 61

In water (7 ml) was dissolved 7β-[D-5-(p-t-butylbenzamido)-5-carboxyvaleramido]-3-[2-carboxy-6 (or 3)-nitrobenzoyloxy]methyl-3-cephem-4-carboxylic acid (0.73 g), sodium azide (0.26 g) and sodium hydrogen carbonate (0.25 g). The mixture was stirred at 60° C. for 40 minutes. The reaction mixture was brought to room temperature and, following the addition of 10% aqueous phosphoric acid (10 ml), extracted with ethyl acetate (30 ml). The ethyl acetate layer was washed with a saturated solution of sodium chloride (20 ml), dried over magnesium sulfate and concentrated under reduced pressure. Then, upon addition of ether, there was obtained a powder. This powder was suspended in water (3 ml) and dissolved by the addition of sodium hydrogen carbonate (0.17 g). This solution was subjected to column-chromatography on Sephadex LH-20 (250 ml), elution being carried out with water. The fractions containing the desired product were pooled and lyophilized.

The procedure provided 7β-[D-5-(p-t-butylbenzamido)5-carboxyvaleramido]-3-azidomethyl-3-cephem-4-carboxylic acid disodium salt (0.36 g).

IR(KBr): 2100, 1766, 1606 cm$^{-1}$.

NMR(δin D$_2$O): 1.32(9H,s,—C(CH$_3$)$_3$), 1.92 & 2.48(6H, —(CH$_2$)$_3$—), 3.05 & 3.53 (2H,ABq,J=18 Hz,2—CH$_2$), 4.03 & 4.20(2H, ABq,J=13 Hz,3-CH$_2$), 4.52(1H,—CH—), 5.08(1H,d,J=5 Hz, 6-H), 5.68(1H,d,J=5 Hz,7-H),

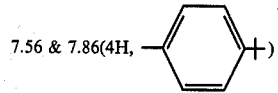
7.56 & 7.86(4H,

EXAMPLE 62

In phosphate buffer (40 ml) of pH 6.4 was dissolved 7-[2-(2-imino-4-thiazolin-4-yl)acetamido]-3-(3-oxobutyryloxy)methyl-3-cephem-4-carboxylic acid (908 mg), together with a nitrogen-containing heterocyclic thiol (2.2 mMol) and sodium hydrogen carbonate (336 mg). The solution was stirred at 60° C. for 1 hour, after which it was concentrated under reduced pressure to about 20 ml. The concentrate was subjected to column-chromatography on Amberlite XAD-2, elution being carried out with water, 5% ethanol and 10% ethanol in the order mentioned. The fractions containing the desired product were pooled and lyophilized to obtain the corresponding one of the following compounds. The reaction yield figure was the value determined by liquid chromatography immediately following the reaction.

(1) 7-[2-(2-Imino-4-thiazolin-4-yl)acetamido]-3-(2-carboxymethyl-1,3,4-thiadiazol-5-yl)thiomethyl-3-cephem-4-carboxylic acid disodium salt; yield 85%.

IR(KBr); 1761 cm$^{-1}$.

NMR(δ in D$_2$O): 3.56 & 3.92(2H,ABq,J=18 Hz,2-CH$_2$), 3.76(2H, s,—CH$_2$CO), 4.16(2H,s,—CH$_2$CO), 4.20 & 4.62(2H,ABq, J=13 Hz,3-CH$_2$), 5.24(1H,d,J=5 Hz,6-H), 5.79(1H,d,J=5 Hz,7-H), 6.65(1H,s,thiazolin-5-H).

(2) 7-[2-(2-1mino-4-thiazolin-4-yl)acetamido]-3-(3-hydroxymethyl-4-methyl-1,2,4-triazol-5-yl)thiomethyl-3-cephem-4-carboxylic acid sodium salt; yield 82%.

IR(KBr): 1760 cm$^{-1}$.

NMR(δ in D$_2$O): 3.40 & 3.82(2H,ABq,J=18 Hz,2—CH$_2$), 3.62 (2H,s,—CH$_2$CO), 3.74(3H,s,—CH$_3$), 3.72 & 4.34(2H, ABq,J=13 Hz,3-CH$_2$), 4.82(2H,s,CH$_2$OH), 5.08(1H,d, J=5 Hz,6-H), 5.64(1H,d,J=5 Hz,7-H), 6.52(1H,s,thiazolin-5-H).

EXAMPLE 63

In 50 ml of water was dissolved 5.61 g of 7-[D-5-(benzamido)adipinamido]-3-(3-oxobutyryloxy)methyl-3-cephem-4-carboxylic acid, together with 1.50 g of 5-mercapto-1-methyl-1H-tetrazole and 2.20 g of sodium bicarbonate. After the pH was adjusted to 5.2, the reaction was carried out at 60° C. for 50 minutes. After cooling, 100 ml of a saturated aqueous solution of sodium chloride was added and the pH was adjusted to pH 1.5 with 4N-HCl. The solid precipitate was recovered by filtration, rinsed with 20 ml of a saturated aqueous solution of sodium chloride and dissolved in 100 ml of ethyl acetate-tetrahydrofuran (2:1) and 20 ml of water. The organic layer was dried and the solvent was distilled off under reduced pressure. To the residue was added ether-ethyl acetate and the resultant powder was recovered by filtration, rinsed with ether and dried. The procedure provided 5.45 g (yield 94.8%) of 7-[D-5-benzamido-5-carboxyvaleramido)-3-(1-methyl-1H-tetrazol-5-yl)thiomethyl-3-cephem-4-carboxylic acid.

IR(KBr): 3340, 1783, 1730, 1645, 1535 cm$^{-1}$.

NMR(δ in d$_6$-DMSO): 1.50–2.0(4H,m), 2.05–2.45(2H,m), 3.70 (2H,broad), 3.93(3H,s,N CH$_3$), 4.15–4.55(3H,m), 5.10 (1H,d,J=5 Hz,6-H), 5.66(1H,dd,J=5 & 9 Hz,7-H),

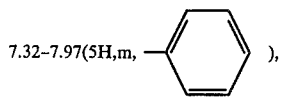
7.32–7.97(5H,m, 8.43(1H,d,J=8 Hz,—CONH—), 8.73 (1H,d J=9 Hz,—CONH—).

EXAMPLE 64

In 50 ml of water was dissolved 6.11 g of 7-[D-5-(p-toluenesulfonamido)adipinamido]-3-(3-oxobutyryloxy)-methyl-3-cephem-4-carboxylic acid, together with 1.50 g of 5-mercapto-1-methyl-1H-tetrazole and 2.20 g of sodium bicarbonate. After the solution was adjusted to pH 5.0, the reaction was conducted at 60° C. for 50 minutes. Following the reaction, the reaction mixture was treated in the same manner as Example 63. The procedure provided 5.96 g (yield 95.1%) of 7-[D-5-(p-toluenesulfonamido)-5-carboxyvaleramido]-3-(1-methyl-1H-tetrazol-5-yl)thiomethyl-3-cephem-4-carboxylic acid.

IR(KBr): 3275, 1780, 1727, 1635, 1535 cm$^{-1}$.

NMR(δ in d$_6$-DMSO): 1.45–1.78(4H,m), 2.0–2.3(2H,m), 2.41 (3H,s,—CH$_3$), 3.71(2H,broad,2-CH$_2$), 3.95(3H,s,—NCH$_3$), 4.28(2H,broad), 5.06(1H,d,J=5 Hz,6-H), 5.62(1H,dd, J=5.0 & 9.0 Hz,7-H),

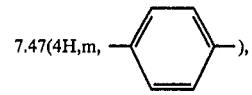
7.47(4H,m, 7.91(1H,d, J=9.0 Hz), 8.68(1H,d,J=9.0 Hz).

EXAMPLE 65

In 50 ml of water was dissolved 6.17 g of 7-[D-5-(p-tert-butylbenzamido)-5-carboxyvaleramido]-3-(3-oxobutyryloxy)methyl-3-cephem-4-carboxylic acid, together with 1.74 g of 5-mercapto-1-methyl-1H-tetrazole and 2.50 g of sodium bicarbonate. After the solution was adjusted to pH 5.0, the reaction was conducted at 60° C. for 50 minutes. Following the reaction, the mixture was treated in the same manner as Example 63 to obtain 6.02 g (yield 95.3%) of 7-[D-5-(p-tert-butylbenzamido)-5-carboxyvaleramido]-3-(1-methyl-1H-tetrazol-5-yl)thiomethyl-3-cephem-4-carboxylic acid.

IR(KBr): 3350, 1780, 1725, 1643, 1532, 1504 cm$^{-1}$.

NMR(δ in d$_6$-DMSO): 1.30(9H,s,—C(CH$_3$)$_3$), 1.50–2.45(6H,m, —(CH$_2$)$_3$—), 3.64(2H,broad,2-CH$_2$), 3.93(3H,s,—NCH$_3$), 4.27(2H,broad,3-CH$_2$),

4.36(1H,m,—CH—), 5.0(1H,d, J=5 Hz,6-H), 5.62(1H,dd,J=5.0 & 8.0 Hz,7-H), 7.35(2H, d,J=8.0 Hz), 7.70(2H,d,J=8 Hz), 8.36(1H,d,J=8.0 Hz, —CONH—), 8.76 (1H,d,J=8.0 Hz, —CONH—).

EXAMPLE 66

In 50 ml of water was dissolved 4.83 g of 7-[D-5-(caprylamido)-5-carboxyvaleramido]-3-(3-oxobutyryloxy)methyl-3-cephem-4-carboxylic acid, together with 1.74 g of 5-mercapto-1-methyl-1H-tetrazole and 2.50 g of sodium bicarbonate. After the solution was adjusted to pH 5.0 and 35.0 g of sodium bromide was added, the reaction was conducted at 60° C. for 45 minutes.

Following this reaction period, the reaction mixture was treated in the same manner as Example 63. The procedure provided 4.78 g (yield 96.3%) of 7-[D-5-(caprylamido)-5-carboxyvaleramido]-3-(1-methyl-1H-tetrazol-5-yl)thiomethyl-3-cephem-4-carboxylic acid.

IR(KBr): 3300, 1775, 1725, 1655, 1640, 1545, 1533 cm$^{-1}$.

NMR(δ in d$_6$-DMSO): 0.60–2.40(21H,m), 3.70(2H,broad, 2-CH$_2$), 3.95(3H,s,NCH$_3$), 4.15(1H,m), 4.27(2H,broad, 3-CH$_2$), 5.03(1H,d,J=5 Hz,6-H), 5.65(1H,dd,J=5.0 & 8.0 Hz,7-H), 7.97(1H,d,J=8.0 Hz,—CONH—), 8.76(1H, d,J=8.0 Hz,—CONH—)

EXAMPLE 67

In 50 ml of water was dissolved 4.32 g of 7-phenylacetamido-3-(3-oxobutyryloxy)methyl-3-cephem-4-carboxylic acid, together with 1.50 g of 5-mercapto-1-methyl-1H-tetrazole and 1.68 g of sodium bicarbonate and the reaction was conducted at 60° C. for 50 minutes. After cooling, the reaction mixture was adjusted to pH 5.0 and washed with ethyl acetate. It was then brought down to pH 2.0 and extracted three times with ethyl acetate. The ethyl acetate solution was washed with a saturated aqueous solution of sodium chloride, treated with magnesium sulfate, filtered and distilled under reduced pressure to remove the solvent. The residue was recrystallized from ethyl acetate-ether. The procedure provided 4.29 g (yield 96.2%) of 7-phenylacetamido-3-(1-methyl-1H-tetrazol-5-yl)thiomethyl-3-cephem-4-carboxylic acid.

IR(KBr): 3270, 1785, 1733, 1662, 1628, 1542 cm$^{-1}$.

NMR($\delta$ in d$_6$-DMSO): 3.55(2H,s,—CH$_2$CO—), 3.60(2H,broad,2-CH$_2$), 3.92(3H,s,NCH$_3$), 4.26(2H,broad,3-CH$_2$), 5.00(1H,d, J=5.0 Hz,6-H), 5.60(1H,dd,J=5.0 & 8.0 Hz,7-H),

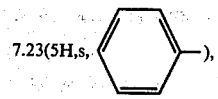

8.98(1H,d,J=8 Hz,—CONH—).

EXAMPLE 68

In 10 ml of water was dissolved 561 mg of 7-[D-5-benzamido-5-carboxyvaleramido]-3-(3-oxobutyryloxy)-methyl-3-cephem-4-carboxylic acid, together with 252 mg of sodium bicarbonate and 212 mg of 2-methylthio-5-mercapto-1,3,4-thiadiazole. The reaction was conducted at 60° C. for 50 minutes and, after cooling, the reaction mixture was washed with ethyl acetate and freeze-dried. The resultant solid was dissolved in a small quantity of methanol and treated with acetone. The crystals formed were collected by filtration and rinsed with ether. The procedure provided 614 mg of 7-[D-5-benzamido-5-carboxyvaleramido]-3-(2-methylthio-1,3,4-thiadiazol-5-yl)thiomethyl-3-cephem-4-carboxylic acid disodium salt.

IR(KBr): 3400, 1766, 1640, 1600, 1530 cm$^{-1}$.

NMR($\delta$ in D$_2$O): 1.40-2.55(6H,m,—(CH$_2$)$_3$—), 2.68(3H,s,SCH$_3$), 3.33(2H,ABq,J=18 Hz,2-CH$_2$), 4.14(2H,ABq,J=14 Hz,3-CH$_2$), 4.30(1H,m,—CH—),
$\quad\quad\quad\quad\quad\quad |$ 5.01(1H,d,J=4.5 Hz,6-H), 5.58(1H,d, J=4.5 Hz,7-H),

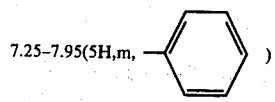

EXAMPLE 69

In 10 ml of water was dissolved 561 mg of 7-[D-5-benzamido-5-carboxyvaleramido]-5-(3-oxobutyryloxy)-methyl-3-cephem-4-carboxylic acid, together with 252 mg of sodium carbonate and 224 mg of 5-mercapto-2-ethoxycarbonylmethyl-1H-1,3,4-triazole. The reaction was conducted at 60° C. for 50 minutes and, after cooling, the reaction mixture as treated in the same manner as Example 68. The procedure provided 642 mg of 7-[D-5-benzamido-5-carboxyvaleramido]-3-(2-ethoxycarbonylmethyl-1H-1,3,4-triazol-5-yl)thiomethyl-3-cephem-4-carboxylic acid disodium salt.

IR(KBr): 3400, 3280, 1765, 1745, 1640, 1603, 1535 cm$^{-1}$.

NMR($\delta$ in D$_2$O): 1.20(3H,t,J=8.0 Hz,—CH$_2$CH$_3$), 1.50-2.50(6H,m, —(CH$_2$)$_3$—), 3.32(2H,ABq,J=19 Hz,2-CH$_2$), 3.80-4.50(7H, m), 4.95(1H,d,J=4.5 Hz,6-H), 5.52(1H,d,J=4.5 Hz,7-H),

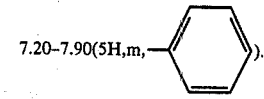

EXAMPLE 70

In 12 ml of water was dissolved 1.27 g of 7$\beta$-[D-5-(p-t-butylbenzamido)-5-carboxyvaleramido]-3-(3-carboxypropionyloxy)methyl-3-cephem-4-carboxylic acid, together with 0.25 g of 5-mercapto-1-methyl-1H-tetrazole and 0.68 g of sodium hydrogen carbonate, followed by the stirring for one hour and a half at 60° C. The reaction solution was allowed to be cooled at the room temperature and added 30 ml of 4% aqueous solution of phosphoric acid, followed by extracting with 60 ml of ethyl acetate. The ethyl acetate layer was washed with a saturated aqueous solution of sodium chloride (40 ml×2) and dried over magnesium sulfate, followed by condensation under reduced pressure. The condensate was added ether and the resultant powder was recovered by filtration, washed with ether and dried over phosphorous pentoxide under reduced pressure to give 1.02 g of 7$\beta$-[D-(5-(p-t-butylbenzamido)-5-carboxyvaleramido]-3-(1-methyl-1H-tetrazol-5-yl)thiomethyl-3-cephem-4-carboxylic acid.

In IR and NMR spectra, this product was found in good agreement with the product obtained in Example 65.

EXAMPLE 71

In 12 ml of water were dissolved 1.26 g of 7$\beta$-[D-5-(p-t-butylbenzamido)-5-carboxyvaleramido]-3-(3-carboxyacryloxy)methyl-3-cephem-4-carboxylic acid, 0.25 g of 5-mercapto-1-methyl-1H-tetrazole and 0.68 g of sodium hydrogen carbonate, and the solution was stirred for 2 hours at 60° C., followed by the treatment in the same manner as Example 70. The procedure provided 0.88 g of 7$\beta$-[D-5-(p-t-butylbenzamido)-5-carboxyvaleramido]-3-(1-methyl-1H-tetrazol-5-yl)thiomethyl-3-cephem-4-carboxylic acid, of which IR and NMR were found in good agreement with that of the product obtained in Example 65.

EXAMPLE 72

The reaction of Example 71 was repeated employing 1.36 g of 7$\beta$-[D-5-(p-t-butylbenzamido)-5-carboxyvaleramido]-3-(2-carboxybenzoyloxy)methyl-3-cephem-4-carboxylic acid. The procedure provided 0.97 g of 7$\beta$-[D-5-(p-t-butylbenzamido)-5-carboxyvaleramido]-3-(1-methyl-1H-tetrazol-5-yl)thiomethyl-3-cephem-4-carboxylic acid, of which IR and NMR were found in good agreement with that of the product obtained in Example 65.

EXAMPLE 73

In 12 ml of water were dissolved 1.55 g of 7$\beta$-[D-5-(p-t-butylbenzamido)-5-carboxyvaleramido]-3-[3-carboxy-3 (or 2)-(p-chlorophenylthio)propionyloxy]methyl-3-cephem-4-carboxylic acid, 0.25 g of 5-mercapto-1- methyl-1H-tetrazole and 0.68 g of sodium hydrogen carbonate, and the solution was stirred for one hour and a half at 60° C., followed by the treatment in the same manner as Example 70. The procedure provided 0.99 g of 7β-[D-L5-(p-t-butylbenzamido)-5-carboxyvaleramido]-3-(1-methyl-1H-tetrazol-5-yl)thiomethyl-3-cephem-4-carboxylic acid, of which IR and NMR were found in good agreement with that of the product obtained in Example 65.

EXAMPLE 74

The reaction of Example 73 was repeated employing 1.21 g of 7β-(D-5-phthalimido-5-carboxyvaleramido)-3-(3carboxypropionyloxy)methyl-3-cephem-4-carboxylic acid. The procedure provided 1.00 g of 7β-(D-5-phthalimido-5-carboxyvaleramido)-3-(1-methyl-1H-tetrazol-5-yl)thiomethyl-3-cephem-4-carboxylic acid, of which IR and NMR were found in good agreement with that of the product obtained in Example 1 (2).

EXAMPLE 75

The reaction of Example 73 was repeated employing 1.30 g of 7β-(D-5-phthalimido-5-carboxyvaleramido)-3-(2-carboxybenzoyloxy)methyl-3-cephem-4-carboxylic acid. The procedure provided 0.94 g of 7β-(D-5-phthalimido-5-carboxyvaleramido)-3-(1-methyl-1H-tetrazol-5-yl)thiomethyl-3-cephem-4-carboxylic acid, of which IR and NMR were found in good agreement with that of the product obtained in Example 1 (2).

EXAMPLE 76

In water (6 ml) was dissolved 7β-[D-5-(2-carboxy-6 (or 3)-nitrobenzamido)-5-carboxyvaleramido]-3-(2-carboxy-6(or 3)-nitrobenzoyloxy)methyl-3-cephem-4-carboxylic acid (0.78 g) together with 5-mercapto-1-methyl-1H-tetrazole (0.12 g) and sodium hydrogen carbonate (0.42 g). The solution was stirred at 60° C. for 30 minutes, after which time it was treated as in Example 70. The procedure provided 7β-[D-5-(2-carboxy-6 (or 3)-nitrobenzamido)-5-carboxyvaleramido]-3-(1-methyl-1H-tetrazol-5-yl)thiomethyl-3-cephem-4-carboxylic acid (0.50 g).

IR(KBr): 1782, 1731, 1645, 1537, 1351 cm$^{-1}$.

NMR(d$_6$-DMSO): δ1.73 & 2.26(6H,—(CH$_2$)$_3$—), 3.69(2H,2—CH$_2$), 3.94(3H,s, >N—CH$_3$), 4.32(2H,3—CH$_2$), 4.52(1H,—CH—),
|

5.06(1H,d,J=5 Hz,6-H), 5.67(1H,dd,J=5 & 8 Hz,7-H),

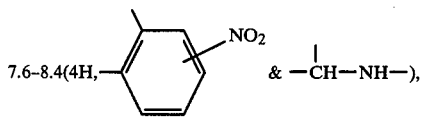
& —CH—NH—),
|

8.79(1H,d,J=8 Hz, —CONH—).

EXAMPLE 77

In water (6 ml) was dissolved 7β-[D-5-(p-t-butylbenzamido)-5-carboxyvaleramido]-3-(2-carboxy-6(or 3)-nitrobenzoyloxy)methyl-3-cephem-4-carboxylic acid (0.73 g) together with 5-mercapto-1-methyl-1H-tetrazole (0.12 g) and sodium hydrogen carbonate (0.34 g). The mixture was stirred at 60° C. for 30 minutes, after which time it was treated as in Example 70. The procedure provided 7β-[D-5-(p-t-butylbenzamido)-5-carboxyvaleramido]-3-(1-methyl-1H-tetrazol-5-yl)thiomethyl-3-cephem-4-carboxylic acid (0.53 g).

In IR(KBr) and NMR(d$_6$-DMSO) spectra, this compound was in good agreement with the product obtained in Example 65.

EXAMPLE 78

The reaction of Example 76 was repeated employing 0.73 g of 7β-[D-5-(p-t-butylbenzamido)-5-carboxyvaleramido]-3-(2,4 (or 5)-dicarboxybenzoyloxy)methyl-3-cephem-4-carboxylic acid to give 0.52 g of 7β-[D-5-(p-t-butylbenzamido)-5-carboxyvaleramido]-3-(1-methyl-1H-tetrazol-5-yl)thiomethyl-3-cephem-4-carboxylic acid. In IR(KBr) and NMR(d$_6$-DMSO) spectra, this compound was in good agreement with the product in Example 65.

EXAMPLE 79

In water (6 ml) was dissolved 7β-(D-5-phthalimido-5-carboxyvaleramido)-3-(2-carboxy-6 (or 3)-nitrobenzoyloxy)methyl-3-cephem-4-carboxylic acid (0.70 g) together with 5-mercapto-2-methyl-1,3,4-thiadiazole (0.13 g) and sodium hydrogen carbonate (0.34 g). The solution was stirred at 60° C. for 30 minutes, after which time it was treated as in Example 65. The procedure provided 7β-(D-5-phthalimido-5-carboxyvaleramido)-3-(2-methyl-1,3,4-thiadiazol-5-yl)thiomethyl-3-cephem-4-carboxylic acid (0.51 g).

IR(KBr): 1773(sh), 1715, 1648(sh)cm$^{-1}$.

NMR(d$_6$-DMSO): δ1.53 & 2.15(6H, —(CH$_2$)$_3$—), 2.67(3H,s, —CH$_3$), 3.45 & 3.72(2H, ABq,J=18 Hz, 2-CH$_2$), 4.19 & 4.50(2H, ABq,J=13 Hz,3-CH$_2$), 4.72(1H,t,J = 7Hz,—CH—),
|

5.02(1H, d,J=5 Hz, 6-H), 5.61(1H,dd,J=5 & 8 Hz,7-H),

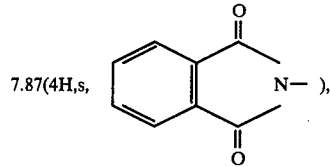

8.74(1H,d,J=8 Hz, —CONH—).

EXAMPLE 80

The reaction of Example 79 was repeated employing 0.73 g of 7β-[D-5-(p-t-butylbenzamido)-5-carboxyvaleramido]-3-(2-carboxy-6(or 3)-nitrobenzoyloxy)-methyl-3-cephem-4-carboxylic acid to give 0.55 g of 7β-[D-5-(p-t-butylbenzamido)-5-carboxyvaleramido]-3-(2-methyl-1,3,4-thiadiazol-5-yl)thiomethyl-3-cephem-4-carboxylic acid.

IR(KBr): 1780, 1728, 1644 cm$^{-1}$.

NMR(d$_6$-DMSO): δ1.28(9H,s,—C(CH$_3$)$_3$), 1.74 & 2.23 (6H,—(CH$_2$)$_3$—), 2.66(3H,s,—CH$_3$), 3.50 & 3.75(2H,ABq,J=18 Hz,2-CH$_2$), 4.20 & 4.50(2H,ABq,J=13 Hz,3-CH$_2$), 4.39(1H,—CH—), 5.05(1H,d,J=5 Hz,6-H), 5.65(1H,dd,J=5 & 8 Hz,7-H,

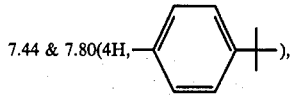
7.44 & 7.80(4H, 8.42(1H,d,J = 8Hz,—CH—NH—), 8.80(1H,d,J=8 Hz,—CONH—).

EXAMPLE 81

In water (5 ml) was dissolved 7β-(D-mandelamido)-3-(3-carboxypropionyloxy)methyl-3-cephem-4-carboxylic acid (0.46 g) together with 5-mercapto-1-methyl-1H-tetrazole (0.12 g) and sodium hydrogen carbonate (0.25 g). The solution was stirred at 60° C. for 1 hour and a half. After cooling in the air, the reaction mixture was subjected to column chromatography on Amberlite XAD-2, elution being carried out with water and, then, with a solvent mixture of water and methanol. The fractions containing the desired compound are pooled, concentrated and lyophilized. The procedure provided 7β-(D-mandelamido)-3-(1-methyl-1H-tetrazol-5-yl)thiomethyl-3-cephem-4-carboxylic acid sodium salt (0.31 g).

IR(KBr): 1761, 1675, 1604 cm$^{-1}$.

NMR(D$_2$O): δ3.25 & 3.68(2H,ABq,J=18 Hz,2-CH$_2$), 3.95(3H,s,>N—CH$_3$), 4.02 & 4.29(2H,ABq,J=13 Hz,3-CH$_2$), 4.97(1H,d,J=5 Hz,6-H), 5.18(1H,s,—CH—), 5.51(1H,d,J=5 Hz,7-H,

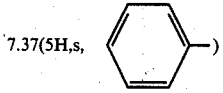
7.37(5H,s,

EXAMPLE 82

In water (5 ml) was dissolved 7β-(2-thienylacetamido)-3-(2-carboxybenzoyloxy)methyl-3-cephem-4-carboxylic acid (0.50 g) together with sodium hydrogen carbonate (0.17 g), potassium iodide (0.40 g) and pyridine (0.21 g). The solution was adjusted to pH 6.5 and, then, stirred at 60° C. for one hour and a half. After cooling in the air, the reaction mixture was subjected to column chromatography on Amberlite XAD-2, elution being carried out with water and, then, with a solvent mixture of water and methanol. The fractions containing the desired product were pooled, concentrated and lyophilized.

The procedure provided 7β-(2-thienylacetamido)-3-(1-pyridylmethyl)-3-cephem-4-carboxylic acid betaine (0.23 g).

IR(KBr): 1763, 1698, 1617 cm$^{-1}$.

NMR(D$_2$O): δ3.17 & 3.67(2H,ABq,J=17 Hz,2-CH$_2$), 3.38(2H,s,—CH$_2$CO—), 5.19(1H,d,J=5 Hz,6-H), 5.41 & 5.67(2H,ABq,J=14 Hz,3-CH$_2$), 5.75(1H,d,J=5 Hz,7-H),

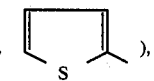
7.01 & 7.28(3H,

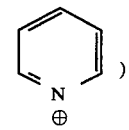
8.15 & 8.62 & 9.04(5H,

EXAMPLE 83

The following compounds were synthesized by procedures similar to that described in Example 79.

(1) 7β-(D-5-Phthalimido-5-carboxyvaleramido)-3-[2-(2-hydroxyethylthio)-1,3,4-thiadiazol-5-yl]thiomethyl-3-cephem-4-carboxylic acid.

IR(KBr): 3325, 1780, 1715, 1645, 1530 cm$^{-1}$.

NMR(d$_6$-DMSO): δ1.30–2.40(m,6H), 3.20–3.80(m,6H), 4.27 (AB-q, 2H,J=12 Hz), 4.65(t,1H,J=9 Hz), 4.96(d,1H,J=5Hz), 5.55(q,1H,J=5 & 8 Hz), 7.87(s,4H), 8.70 (d,1H,J=8 Hz).

(2) 7β-(D-5-Phthalimido-5-carboxyvaleramido)-3-(2-carbamoylmethylthio-1,3,4-thiadiazol-5-yl)thiomethyl-3-cephem-4-carboxylic acid.

IR(KBr): 3430, 3340, 1776, 1717, 1680, 1535, cm$^{-1}$.

NMR(d$_6$-DMSO): δ1.30–2.40(m,6H), 3.57(broad,2H), 4.40(s,2H), 4.32(AB-q, 2H,J=12 Hz), 4.70(t,1H,J=8.0 Hz), 5.0(d,1H,J=5 Hz), 5.55(q,1H,J=5 & 8 Hz), 7.20 (br.1H), 7.60(br.1H), 7.86(s,4H), 8.74(d,1H,J=5 Hz).

EXAMPLE 84

7β-(2-Thienylacetamido)-3-(1-methyl-1H-tetrazol-5-yl)thiomethyl-3-cephem-4-carboxylic acid was prepared by the procedure similar to that described in Example 81. Yield 0.37 g starting from 0.50 g of 7β-(2-thienylacetamido)-3-(2-carboxybenzoyloxy)methyl-3-cephem-4-carboxylic acid.

IR(KBr): 1776, 1734, 1672 cm$^{-1}$.

NMR(d$_6$-DMSO): δ3.56 & 3.78(2H,ABq,J=18 Hz,2-CH$_2$), 3.73 (2H,s,—CH$_2$CO—), 3.92(3H,s, >N—CH$_3$), 4.21 & 4.37(2H,ABq,J=13 Hz,3-CH$_2$), 5.05(1H,d,J=5 Hz,6-H), 5.66(1H,dd,J=5 & 8 Hz,7-H),

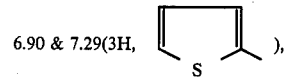
6.90 & 7.29(3H, 9.10(1H,d,J=8 Hz,—CONH—).

EXAMPLE 85

In water (12 ml) was dissolved 7β-[D-5-(p-t-butylbenzamido)-5-carboxyvaleramido]-3-mandelyloxymethyl-3-cephem-4-carboxylic acid (1.33 g) together with 5-mercapto-1-methyl-1H-tetrazole (0.25 g) and sodium hydrogen carbonate (0.51 g). The mixture was stirred at 60° C. for 30 minutes, after which time it was brought down to room temperature. Following the addition of 4% aqueous phosphoric acid solution (30 ml), the reaction mixture was extracted with ethyl acetate (60 ml). The ethyl acetate layer was washed with a saturated aqueous solution of sodium chloride (40 ml×2), dried (over magnesium sulfate) and concentrated under reduced pressure. Then, upon addition of ether, there was obtained a powder. This powder was recovered by filtration, washed with ether and dried under reduced pressure over phosphorus pentoxide. The procedure provided 7β-[D-5-(p-t-butylbenzamido)-5-carboxyvaleramido]-3-(1-methyl-1H-tetrazol-5-yl)thiomethyl-3-cephem-4-carboxylic acid (1.14 g).

In IR(KBr) and NMR(d₆-DMSO) spectra, this compound was good agreement with the product in Example 65.

EXAMPLE 86

In water (12 ml) was dissolved 7β-(D-5-phthalimido-5-carboxyvaleramido)-3-mandelyloxymethyl-3-cephem-4-carboxylic acid (1.27 g) together with 5-mercapto-1-methyl-1H-tetrazole (0.25 g) and sodium hydrogen carbonate (0.51 g). The solution was stirred at 60° C. for 30 minutes. After the reaction had been completed, the reaction mixture was treated in the same manner as Example 85. The procedure provided 7β-(D-5-phthalimido-5-carboxyvaleramido)-3-(1-methyl-1H-tetrazol-5-yl)thiomethyl-3-cephem-4-carboxylic acid (1.12 g).

In IR(KBr) and NMR(d₆-DMSO) spectra, this compound was good agreement with the product in Example 1 (3).

EXAMPLE 87

In water (5 ml) was dissolved 7β-(D-mandelamido)-3-mandelyloxymethyl-3-cephem-4-carboxylic acid (0.50 g) together with 5-mercapto-1-methyl-1H-tetrazole (0.12 g) and sodium hydrogen carbonate (0.17 g). The solution was stirred at 60° C. for 30 minutes. After cooling in the air, the reaction mixture was subjected to column chromatography on Amberlite XAD-2, elution being carried out with water and a solvent mixture of water and methanol. The fractions containing the desired product were pooled, concentrated and lyophilized. The procedure provided 7β-(D-mandelamido)-3-(1-methyl-1H-tetrazol-5-yl)thiomethyl-3-cephem-4-carboxylic acid sodium salt (0.34 g).

In IR and NMR spectra, this compound was good agreement with the product in Example 81.

EXAMPLE 88

In water (5 ml) was dissolved 7β-(2-thienylacetamido)-3-mandelyloxymethyl-3-cephem-4-carboxylic acid (488 mg) together with sodium hydrogen carbonate (84 mg), potassium iodide (400 mg) and pyridine (212 mg). The solution was adjusted to pH 6.5 and reacted at 60° C. for 45 minutes. After cooling, the reaction mixture was subjected to column chromatography on Amberlite XAD-2, elution being carried out with water and, then, a solvent mixture of water and methanol. The fractions containing the desired product were pooled, concentrated and lyophilized. The procedure provided 7β-(2-thienylacetamido)-3-(1-pyridylmethyl)-3-cephem-4-carboxylic acid betaine (250 mg).

In IR and NMR spectra, this compound was good agreement with the product in Example 82.

EXAMPLE 89

In water (4 ml) was dissolved 7β-(2-thienylacetamido)-3-mandelyloxymethyl-3-cephem-4-carboxylic acid (0.49 g) together with 5-mercapto-1-methyl-1H-tetrazole (0.12 g) and sodium hydrogen carbonate (0.17 g). The solution was stirred at 60° C. for 30 minutes. After the reaction had been completed, the reaction mixture was treated by a procedure similar to that described in Example 85. The procedure provided 7β-(2-thienylacetamido)-3-(1-methyl-1H-tetrazol-5-yl)thiomethyl-3-cephem-4-carboxylic acid (0.40 g).

In IR and NMR spectra, this compound was good agreement with the product in Example 84.

EXAMPLE 90

The following compounds were synthesized by procedures similar to those described in Example 85 and 86.
(1) 7β-[D-5-(p-t Butylbenzamido)-5-carboxyvaleramido]-3-(2-methyl-1,3,4-thiadiazol-5-yl)thiomethyl-3-cephem-4-carboxylic acid. Yield 84%.

In IR and NMR spectra, this compound was good agreement with the product in Example 80.
(2) 7β-(D-5-Phthalimido-5-carboxyvaleramido)-3-(2-methyl-1,3,4-thiadiazol-5-yl)thiomethyl-3-cephem-4-carboxylic acid. Yield 86%.

In IR and NMR spectra, this compound was good agreement with the product in Example 79.
(3) 7β-(D-5-Phthalimido-5-carboxyvaleramido)-3-[2-(2-hydroxyethylthio)-1,3,4-thiadiazol-5-yl]thiomethyl-3-cephem-4-carboxylic acid. Yield 81%.

In IR and NMR spectra, this compound was good agreement with the product in Example 83 (1).
(4) 7β-(D-5-Phthalimido-5-carboxyvaleramido)-3-(2-carbamoylmethylthio-1,3,4-thiadiazol-5-yl)thiomethyl-3-cephem-4-carboxylic acid. Yield 88%.

In IR and NMR spectra, this compound was good agreement with the product obtained in Example 83(2).

EXAMPLE 91

In water (30 ml) were dissolved 7β-amino-3-(3-oxobutyryloxy)methyl-3-cephem-4-carboxylic acid (3.14 g), sodium hydrogen carbonate (1.84 g) and 5-mercapto-1-methyl-1H-tetrazole (1.4 g) and the solution was adjusted its pH to 5.5, followed by stirring and heating at 60° C. for one hour. After cooling, the reaction solution was washed with dichloromethane (20 ml) and the aqueous layer was adjusted to pH 3.3, followed by stirring for one hour under ice-cooling. The resultant precipitates were collected by filtration and washed with water, methanol and acetone in this order, followed by drying to give 7β-amino-3-(1-methyl-1H-tetrazol-5-yl)thiomethyl-3-cephem-4-carboxylic acid (2.7 g).

IR(KBr): 1795 cm⁻¹.
NMR (δ in D₂O+NaHCO₃): 3.61 & 3.98(2H,ABq,J=18 Hz,2—CH₂), 4.21(s,—NCH₃), 5.21(d,J=4.5 Hz,6-H), 5.60(d,J=4.5 Hz,7-H).

EXAMPLE 92

In water (30 ml) were dissolved 7β-amino-3-(3-oxobutyryloxy)methyl-3-cephem-4-carboxylic acid (3.14 g), sodium hydrogen carbonate (0.84 g) and 5-mercapto-1-[2-(N,N-dimethylamino)ethyl]-1H-tetrazole (2.60 g) and the resultant solution was stirred for 60 minutes at 55° C. After cooling, acetone (15 ml) was added to the reaction solution and the mixture is passed through a column of active alumina (10 g). The column was washed with wateracetone (1:1) (30 ml) and the washing was combined with the eluate, followed by distilling off acetone under reduced pressure. To the residual solution was added Amberlite IR-120 (acid form) (6.0 ml) and the mixture was stirred for 30 minutes under ice-cooling. The insolubles were filtered off and the filtrate was condensed. The condensate was added dropwise into ethanol about 30 times volume of the condensate and precipitated solid was collected by filtration, followed by washing with ethanol and drying to give 7β-amino-3-1-[2-(N,N-dimethylamino)ethyl]-1H-tetrazol-5-yl thiomethyl-3-cephem-4-carboxylic acid (3.28 g).

IR(KBr): 3450, 1780, 1620, 1540 cm$^{-1}$.

NMR (δ in D$_2$O): 3.07(6H,s), 3.70(2H,ABq,J=17 Hz), 3.85(2H,t,J=6 Hz), 4.25(2H,ABq,J=12 Hz), 4.8–5.2(4H,m).

EXAMPLE 93

In water (30 ml) was dissolved 7β-amino-3-(3-oxobutyryloxy)methyl-3-cephem-4-carboxylic acid (3.14 g) together with sodium hydrogen carbonate (1.84 g) and 2-mercapto-5-methyl-1,3,4-thiadiazole (1.6 g) and the resultant solution was adjusted its pH to 6.4, followed by stirring for one hour at 60° C. After cooling, the reaction solution was washed with dichloromethane and pH of the aqueous layer was adjusted to 3.5 under ice-cooling, followed by stirring for one hour. The precipitated materials were collected by filtration and washed with water, methanol and acetone in this order, followed by drying to give 7β-amino-3-(2-methyl-1,3,4-thiadiazol-5-yl)thiomethyl-3-cephem-4-carboxylic acid (2.9 g).

IR(KBR): 1795 cm$^{-1}$.

NMR(δ in D$_2$O+NaHCO$_3$): 2.87(3H,s,thiadiazole—CH$_3$), 3.53 & 3.95(2H,ABq,J=18 Hz,2-CH$_2$), 4.10 & 4.46 (2H,ABq,J=13 Hz,3-CH$_2$), 5.17(1H,d,J=4.5 Hz,6-H), 5.58(1H,d,J=4.5 Hz,7-H).

EXAMPLE 94

In water (1 ml) containing sodium salt of 5-mercapto-1H-1,2,3-triazole (120 mg) and sodium hydroxide (40 mg) was dissolved under ice-cooling 7β-amino-3-(3-oxobutyryloxy)methyl-3-cephem-4-carboxylic acid (282 mg) and to the resultant solution was added 1N-HCl to adjust its pH to 5.5 under stirring, followed by further stirring for one hour at 55° C. To the reaction solution was added methanol (5 ml) and the mixture was allowed to cool to the room temperature. The cooled mixture is adjusted its pH to 3.9 by adding 1N-HCl under stirring and the resultant mixture was further stirred for one hour under ice-cooling. The precipitated insolubles were collected by filtration and washed with water and methanol in this order. The insolubles were dried naturally and then over phosphorus pentoxide to give 7β-amino-3-(1H-1,2,3-triazol-5-yl)thiomethyl-3-cephem-4-carboxylic acid (190 mg).

IR(KBr): 1800, 1525 cm$^{-1}$.

EXAMPLE 95

In water (1 ml) containing sodium hydrogen carbonate (84 mg) was dissolved 7β-amino-3-(3-oxobutyryloxy)methyl-3-cephem-4-carboxylic acid (314 mg) and to the resultant solution were added isonicotinamide (185 mg) and potassium iodide (1.0 g), followed by stirring for one hour at 55° C. To the reaction mixture was added ethanol (20 ml) under stirring and resulting precipitates were collected by filtration, followed by washing with ethanol. After natural drying, the brown power was dissolved in water (3 ml) and the solution was chromatographed on column packed with Amberlite XAD-2. The eluate was freeze-dried to give 7β-amino-3-(4-carbamoylpyridinium)methyl-4-carboxylate (150 mg).

IR(KBr): 3500, 1760, 1600 cm$^{-1}$.

EXAMPLE 96

In a mixture of tetrahydrofuran (5 ml) and water (10 ml) were dissolved 7β-(2-thienylacetamido)-3-(3-oxobutyryloxy)methyl-3-cephem-4-carboxylic acid (876 mg) and sodium sulfite (504 mg) and the resultant solution was stirred for 120 minutes at 60° C. To the reaction mixture was added water (10 ml) and the mixture was adjusted its pH to 7.2 with 2N-HCl, followed by condensation under reduced pressure. The residue was subjected to column-chromatography of silica-gel and eluted with acetonitrile-water (7:1–5:1). The fractions containing the objective compound were combined and the mixture was subjected to distillation of acetonitrile. The residue was chromatographed on column packed with Amberlite XAD-2 and eluted with water and then water-methanol. The fractions containing the objective compound were combined and the mixture was condensed under reduced pressure, followed by freeze-drying to give disodium salt of 7β-(2-thienylacetamido)-3-sulfomethyl-3-cephem-4-carboxylic acid (310 mg).

IR(KBr): 3450, 1760, 1665, 1605, 1190, 1055 cm$^{-1}$.

NMR(δ in D$_2$O): 3.67(2H,ABq,J=17 Hz), 3.92(2H,s), 4.16(2H,ABq,J=16 Hz), 5.20(1H,d,J=5 Hz), 5.64(1H,d,J=5 Hz), 7.05 & 7.40(3H,m).

EXAMPLE 97

In 50 ml of dichloromethane was dissolved 7.05 g of 7-[L-phthalimido-5-carboxyvaleramido]-3-hydroxymethyl-3-cephem-4-carboxylic acid ditriethylamine salt and, at 0° C., triethylamine (1.5 ml) was added to the solution, followed by dropping diketene (2.0 ml) during 10 minutes at −5°–0° C. The mixture was further stirred for 50 minutes at −5°–0° C. and added 40 ml of water, followed by adjusting its pH to 6.0 with 2N-HCl. The aqueous layer was washed with dichloromethane (10 ml) and 2.25 g of 5-mercapto-1-[2-(N,N-dimethylamino)ethyl]-1H-tetrazole was added thereto, followed by adjusting to pH 5.5. The solution was stirred at 60° C. for 40 minutes, and then the insolubles were filtered off. To the filtrate were added sodium chloride (15.0 g) and a saturated aqueous solution of sodium chloride (50 ml) and the mixture was adjusted to pH 2.0 with 4N-HCl. The solid materials precipitated were collected by filtration and washed with a saturated aqueous solution of sodium chloride and water in this order, followed by drying to give 6.75 g of 7β-(D-5-phthalimido-5-carboxyvaleramido)-3-{1-[2-(N,N-dimethylamino)ethyl]-1H-tetrazol-5-yl}thiomethyl-3-cephem-4-carboxylic acid hydrochloride.

IR(KBr): 3370, 1775, 1715, 1640 cm$^{-1}$.

NMR(δ in d$_6$-DMSO): 1.30–2.40(6H,m), 3.5–4.8(9H,m), 5.04 (1H,d,J=5 Hz), 5.60(1H,q,J=5.8 Hz), 7.90(4H,s), 8.86 (1H,d,J=8 Hz).

EXAMPLE 98

In a phosphate buffer solution of pH 6.4 (3 ml) were dissolved 5-mercapto-2-methyl-1,3,4-thiadiazole (79 mg), sodium hydrogen carbonate (50 mg) and 7β-[2-(1H-tetrazol-1-yl)acetamido]-3-(3-carboxypropionyloxy)-methyl-3-cephem-4-carboxylic acid disodium salt (243 mg) and the resultant solution was heated for one hour at 60° C. After cooling, the reaction solution was concentrated under reduced pressure and the residue was subjected to column-chromatography on Sephadex LH-20(250 ml), elution being carried out with water.

The fractions containing the desired product were pooled and lyophilized. The procedure provided sodium 7β-[2-(1H-tetrazol-1-yl)-acetamido]-3-(2-methyl-1,3,4-thiadiazol-5-yl)thiomethyl-3-cephem-4-carboxylate.

NMR(δ in D₂O): 2.78(3H,s,—CH₃), 3.60(2H,ABq,J=18 Hz,2—CH₂), 4.25(2H,ABq,J=13 Hz,3—CH₂), 5.12(1H,d,J=4.5 Hz,6-H), 5.58(2H,s,—CH₂CO—), 5.70(1H,d,J=4.5 Hz,7-H), 9.15(1H,s, tetrazole-H).

EXAMPLE 99

In a phosphate buffer of pH 6.4 (3 ml) were dissolved sodium 7β-[D-α-t-butoxycarbonylamino-α-(p-hydroxylphenyl)-acetamido]-3-(3-oxobutyryloxy)methyl-3-cephem-4-carboxylate (280 mg) and sodium salt of 5-mercapto-1H-1,2,3-triazole (120 mg) and the resulting solution was heated at 60° C. for 60 minutes. After cooling down to room temperature, the reaction solution was chromatographed on a column packed with Amberlite XAD-2 and the combined eluates containing the desired product was freeze-dried to give sodium 7β-[D-α-t-butoxycarbonylamino-α-(p-hydroxyphenyl)acetamido]-3-(1H-1,2,3-triazol-5-yl)thiomethyl-3-cephem-4-carboxylate.

IR(KBr): 3400, 1762, 1678 cm⁻¹.

NMR(D₂O): δ 1.46[9H,s,-C(CH₃)₃], 3.00–4.12(4H,m,2—CH₂, 3—CH₂), 5.00(1H,d,J=4.5 Hz,6-H), 5.60(1H,d,J=4.5 Hz, 7-H),

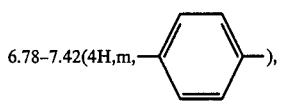

6.78–7.42(4H,m,—⟨ ⟩—), 7.71(1H,s,triazole-4-H).

Thus obtained sodium 7β-[D-α-t-butoxycarbonylamino-α-(p-hydroxyphenyl)acetamido]-3-(1H-1,2,3-triazol-5-yl)-thiomethyl-3-cephem-4-carboxylate (175 mg) was dissolved in formic acid (4 ml) and the resultant solution was stirred for 2 hours at room temperature. The reaction solution was subjected to distillation under reduced pressure and then to azeotropy (3 times) with toluene to remove formic acid, followed by drying over phosphorous pentoxide over night. Thus obtained foamy material was stirred with water-methanol (8:2) (15 ml) and the mixture was subjected to filtration, treatment with activated carbon and then filtration using Celite. The filtrate was freeze-dried to give 7-[D-α-amino-α-(p-hydroxyphenyl)acetamido]-3-(1H-1,2,3-triazol-5-yl)thiomethyl-3-cephem-4-carboxylic acid. This product was in good agreement with the standard in thin-layer chromatography and liquid chromatography.

EXAMPLE 100

In water (10 ml) were dissolved 7β-[2-(2-imino-4-thiazolin-4-yl)acetamido]-3-(3-oxobutyryloxy)methyl-3-cephem-4-carboxylic acid (908 mg), 5-mercapto-1-[2-(N,N-dimethylamino)ethyl]-1H-tetrazole (450 mg) and sodium hydrogen carbonate (168 mg) and the resultant solution was heated at 55° C. for 60 minutes. The reaction solution was revealed to contain 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid in 81% yield relative to the starting cephalosporin by liquid chromatography. The reaction solution was adjusted its pH to 5.8 and purified by column-chromatography using Amberlite XAD-2.

IR(KBr): 1765 cm⁻¹.

NMR(D₂O): δ 3.06(6H,s,—N(CH₃)₂), 3.5–4.8(10H,m), 5.12(1H,d,J=5 Hz,6-H), 5.65(1H,d,J=5 Hz,7-H), 6.62(1H,s,thiazolin-H).

EXAMPLE 101

In dimethylformamide (16.0 ml) was suspended monosodium salt monohydrate of deacetylcephalosporin O(4.13 g) and the resultant suspension was dissolved by adding concentrated hydrochloric acid (1.66 ml) at a temperature lower than 0° C., followed by adding dimethylformamide (16.0 ml), triethylamine (4.90 ml) and phthalic anhydride (2.96 g) in this order. The resultant mixture was stirred for one hour and a half at 20° C. and the reaction solution was poured onto a mixture of an aqueous solution of sodium chloride (200 ml) and dichloromethane (40 ml). The mixture was adjusted its pH to 6.5 and the aqueous layer was separated. The layer was washed with dichloromethane and extracted by a mixed solution of ethyl acetate-tetrahydrofuran (3:1)(50 ml×3) and the combined extract was washed with a saturated aqueous solution of sodium chloride, followed by drying over magnesium sulfate. The dried extract was concentrated under reduced pressure and ether was added to the concentrate. The procedure provided 7β-[D-5-(2-carboxybenzamido)-5-carboxyvaleramido]-3-(2-carboxybenzoyloxy)methyl-3-cephem-4-carboxylic acid (6.22 g).

IR(KBr): 1780, 1735, 1725, 1715, 1640 cm⁻¹.

NMR(δ in d₆-DMSO): 1.40–2.40(6H,m), 2.62(2H,ABq,J=18 Hz), 4.35(1H,m), 5.09(2H,ABq,J=13 Hz), 5.10(1H,d,J=5 Hz), 5.72(1H,dd,J=5 & 8 Hz), 7.30–7.9(8H,m), 8.53(1H,d, J=8 Hz), 8.82(1H,d,J=8 Hz).

What is claimed is:

1. A process for producing a compound of the formula:

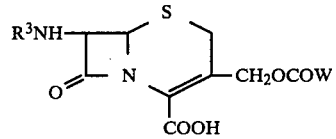

wherein W represents —X—COOH, in which X is a carbon chain which is capable of forming a five- or six-membered ring with

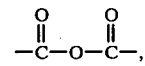

which carbon chain may include a double bond or at least one atom selected from the group consisting of oxygen, nitrogen and sulfur, and on which carbon chain one or more substituents may be attached, the substituent being selected from the group consisting of carboxyl, halogen, nitro, alkyl having up to 3 carbon atoms, aralkyl, aryl, hydroxy substituted by one of said groups and mercapto substituted by one of said groups, and, when two or more of the substituents are present the substituents may form a ring with the carbon chain, and R³ represents an acyl group, or a salt of said compound, which comprises the step of reacting a compound of the formula:

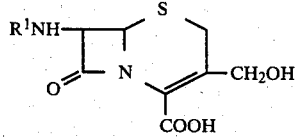

wherein R¹ represents hydrogen or an acyl group, or a salt of said compound, with a compound of the formula:

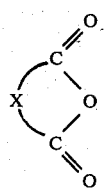

wherein X has the same meaning as defined hereinbefore.

2. A process as claimed in claim 1, wherein 7β-(D-5-phthalimido-5-carboxyvaleramido)-3-hydroxymethyl-3-cephem-4-carboxylic acid or its salt is reacted with succinic anhydride to produce 7β-(D-5-phthalimido-5-carboxyvaleramido)-3-(3-carboxypropionyloxy)methyl-3-cephem-4-carboxylic acid or its salt.

3. A process as claimed in claim 1, wherein 7β-(D-5-phthalimido-5-carboxyvaleramido)-3-hydroxymethyl-3-cephem-4-carboxylic acid or its salt is reacted with phthalic anhydride to produce 7β-(D-5-phthalimido-5-carboxyvaleramido)-3-(2-carboxybenzoyloxy)methyl-3-cephem-4-carboxylic acid or its salt.

4. A process as claimed in claim 1, wherein 7β-(D-α-sulfophenylacetamido)-3-hydroxymethyl-3-cephem-4-carboxylic acid or its salt is reacted with glutaric anhydride to produce 7β-(D-α-sulfophenylacetamido)-3-(4-carboxybutyryloxy)methyl-3-cephem-4-carboxylic acid or its salt.

5. A process as claimed in claim 1, wherein 7β-(D-α-sulfophenylacetamido)-3-hydroxymethyl-3-cephem-4-carboxylic acid or its salt is reacted with succinic anhydride to produce 7β-(D-α-sulfophenylacetamido)-3-(3-carboxypropionyloxy)methyl-3-cephem-4-carboxylic acid or its salt.

6. A process for producing a compound of the formula:

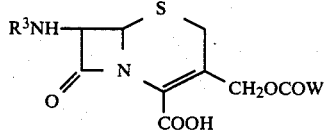

wherein R³ represents an acyl group and W represents —X—OH, in which X is a carbon chain which is capable of forming a five- or six-membered ring with

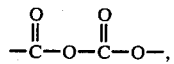

which carbon chain may include a double bond or at least one atom selected from the group consisting of oxygen, nitrogen and sulfur, and on which carbon chain one or more substituents may be attached, the substituent being selected from the group consisting of carboxyl, halogen, nitro, alkyl having up to 3 carbon atoms, aralkyl, aryl, hydroxy substituted by one of said groups and mercapto substituted by one of said groups, and, when two or more of the substituents are present the substituents may form a ring with the carbon chain, or a salt of said compound, which comprises the step of reacting a compound of the formula:

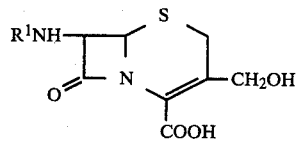

wherein R¹ represents hydrogen or an acyl group, or a salt of said compound, with a compound of the formula:

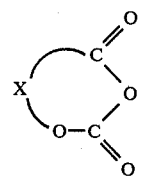

wherein X has the same meaning as defined hereinbefore.

7. A process as claimed in claim 6, wherein 7β-(D-5-phthalimido-5-carboxyvaleramido)-3-hydroxymethyl-3-cephem-4-carboxylic acid or its salt is reacted with O-carboxymandelic anhydride to produce 7β-(D-5-phthalimido-5-carboxyvaleramido)-3-mandelyloxymethyl-3-cephem-4-carboxylic acid or its salt.

8. A process as claimed in claim 6, wherein 7β-[2-(2-imino-4-thiazolin-4-yl)acetamido]-3-hydroxymethyl-3-cephem-4-carboxylic acid or its salt is reacted with O-carboxymandelic anhydride to produce 7β-[2-(2-imino-4-thiazolin-4-yl)acetamido]-3-mandelyloxymethyl-3-cephem-4-carboxylic acid or its salt.

9. A process for producing a compound of the formula:

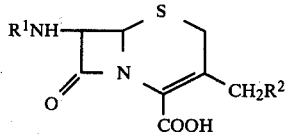

wherein R¹ represents hydrogen or an acyl group and R² represents a residue of a nucleophilic compound, or a salt of said compound, which comprises the step of reacting a compound of the formula:

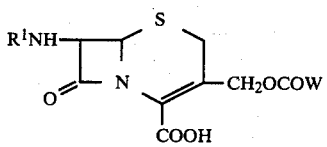

wherein W represents acetonyl, —X—COOH or —X—OH, in which X is a carbon chain which is capable of forming a five- or six-membered ring with

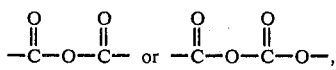

which carbon chain may include a double bond or at least one atom selected from the group consisting of oxygen, nitrogen and sulfur, and on which carbon chain one or more substituents may be attached, the substituents being selected from the group consisting of carboxyl, halogen, nitro, alkyl having up to 3 carbon atoms, aralkyl, aryl, hydroxy substituted by one of said groups and mercapto substituted by one of said groups, and, when two or more of the substituents are present the substituents may form a ring with the carbon chain, and $R^1$ has the same meaning as defined hereinbefore, or a salt of said compound, with a nucleophilic compound.

10. A process as claimed in claim 9, wherein the nucleophilic compound is selected from the group consisting of a nitrogen-containing heterocyclic thiol, an aliphatic thiol, an aromatic thiol, thiourea, a thiourea derivative, a thioamide derivative, sodium thiosulfate, sodium sulfite, potassium thiocyanate, sodium azide, a nitrogen-containing heterocyclic compound, a carbon nucleophilic reagent and an alcohol.

11. A process as claimed in claim 10, wherein the nucleophilic compound is a nitrogen-containing heterocyclic thiol.

12. A process as claimed in claim 10, wherein the nucleophillic compound is a nitrogen-containing heterocyclic compound.

13. A process as claimed in claim 12, wherein the nitrogen-containing heterocyclic compound is pyridine or a pyridine derivative.

14. A process as claimed in claim 13, wherein the pyridine derivative is isonicotinamide.

15. A process for producing a compound of the formula:

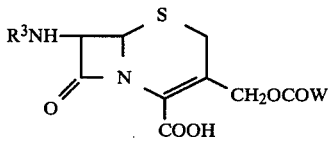

wherein W represents —X—COOH, in which X is a carbon chain which is capable of forming, with

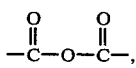

a five- or six-membered ring of the formula

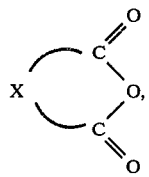

said five- or six-membered ring being maleic anhydride, succinic anhydride, phthalic anhydride, glutaric anhydride, diglycolic anhydride, thiodiglycolic anhydride, p-chlorophenylthiosuccinic anhydride, methylenesuccinic anhydride, 3-nitrophthalic anhydride, trimellitic anhydride or isatoic anhydride, and $R^3$ represents an acyl group, or a salt of said compound, which comprises the step of reacting a compound of the formula:

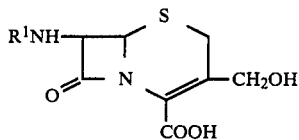

wherein $R^1$ represents hydrogen or an acyl group, or a salt of said compound, with a compound of the formula:

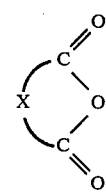

wherein X has the same meaning as defined hereinbefore.

16. A process for producing a compound of the formula:

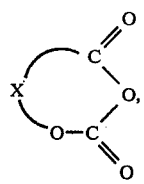

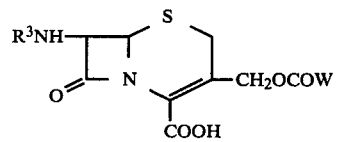

wherein $R^3$ represents an acyl group and W represents —X—OH, in which X is a carbon chain which is capable of forming, with

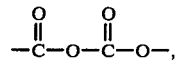

a five- or six-membered ring of the formula

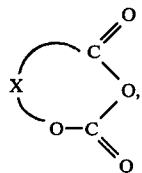

said five- or six-membered ring being O-carboxymandelic anhydride, O-carboxy-α-hydroxypropionic anhydride, O-carboxy-β-hydroxypropionic anhydride, O-carboxy-3-methylsalicylic anhydride, O-carboxy-(α-hydroxy-α-phenyl)propionic anhydride or O-carboxy(α-hydroxy-β-phenyl)propionic anhydride, or a salt of said compound, which comprises the step of reacting a compound of the formula:

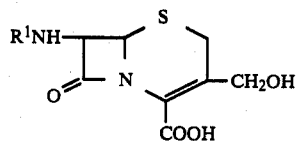

wherein R¹ represents hydrogen or an acyl group, or a salt of said compound, with a compound of the formula:

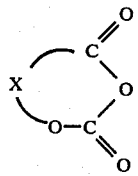

wherein X has the same meaning as defined hereinbefore.

17. A process for producing a compound of the formula:

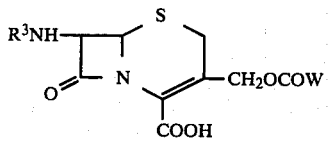

wherein R³ stands for an acyl group and W stands for an acetonyl group, or salt thereof, which comprises the step of reacting a compound of the formula:

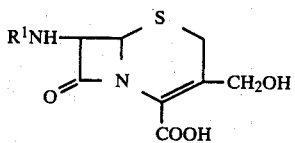

wherein R¹ stands for hydrogen or an acyl group, or salt thereof, with diketene.

18. A process as claimed in claim 17, 1, 6, 9, 15 or 16, wherein each of the symbols R¹ and R³ represents an acyl group of the formula

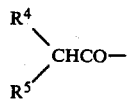

wherein R⁴ represents acetyl, halogenoacetyl, phenyl, p-hydroxyphenyl, thienyl, 2-imino-4-thiazolin-4-yl, 2-oxo-4-thiazolin-4-yl, tetrazolyl, phenoxy or 3-amino-3-carboxypropyl, and R⁵ represents hydrogen, sulfo, amino or hydroxyl, and each amino and carboxyl group in R⁴ and R⁵ may be protected.

19. A process as claimed in claim 18, wherein the protective group for the amino group is selected from the group consisting of phthaloyl, benzoyl, o-carboxybenzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, acetyl, valeryl, capryl, n-decanoyl, acryloyl, pivaloyl, camphorsulfonyl, methanesulfonyl, chloroacetyl, tert-butoxycarbonyl, ethoxycarbonyl, isobornyloxycarbonyl, phenyloxycarbonyl, trichloroethoxycarbonyl, benzyloxycarbonyl, β-methylsulfonylethoxycarbonyl, methylcarbamoyl, phenylcarbamoyl, napthylcarbamoyl and 2-methoxycarbonyl-1-methylvinyl.

20. A process as claimed in claim 18, wherein

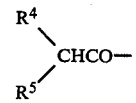

is D-5-amino-5-carboxyvaleryl, the amino group of which is protected by phthaloyl or p-tert-butylbenzoyl, D-α-sulfophenylacetyl or 2-(2-imino-4-thiazolin-4-yl)acetyl.

21. A process as claimed in claim 17, wherein 7β-(5-amino-5-carboxyvaleramido)-3-hydroxymethyl-3-cephem-4-carboxylic acid, the amino group of which is protected, or its salt, is reacted with diketene to produce 7β-(5-amino-5-carboxyvaleramido)-3-(3-oxobutyryloxy)methyl-3-cephem-4-carboxylic acid, the amino group of which is protected, or its salt.

22. A process as claimed in claim 17, wherein 7β-(D-5-phthalimido-5-carboxyvaleramido)-3-hydroxymethyl-3-cephem-4-carboxylic acid or its salt is reacted with diketene to produce 7β-(D-5-phthalimido-5-carboxyvaleramido)-3-(3-oxobutyryloxy)methyl-3-cephem-4-carboxylic acid or its salt.

23. A process as claimed in claim 17, wherein 7β-[D-5-(p-tert-butylbenzamido)-5-carboxyvaleramido]-3-hydroxymethyl-3-cephem-4-carboxylic acid or its salt is reacted with diketene to produce 7β-[D-5-(p-tert-butylbenzamido)-5-carboxyvaleramido]-3-(3-oxobutyryloxy)methyl-3-cephem-4-carboxylic acid or its salt.

24. A process as claimed in claim 17, wherein 7β-(D-α-sulfophenylacetamido)-3-hydroxymethyl-3-cephem-4-carboxylic acid or its salt is reacted with diketene to produce 7β-(D-α-sulfophenylacetamido)-3-(3-oxobutyryloxy)methyl-3-cephem-4-carboxylic acid or its salt.

25. A process as claimed in claim 17, wherein 7β-[2-(2-imino-4-thiazolin-4-yl)acetamido]-3-hydroxymethyl-3-cephem-4-carboxylic acid or its salt is reacted with diketene to produce 7β-[2-(2-imino-4-thiazolin-4-yl)acetamido]-3-(3-oxobutyryloxy)methyl-3-cephem-4-carboxylic acid or its salt.

26. A process as claimed in claim 9, wherein R¹ is D-α-sulfophenylacetyl, W is acetonyl, R² is 4-carbamoylpyridinium and the nucleophilic compound is isonicotinamide.

27. A process as claimed in claim 9, wherein R¹ is D-5-phthalimido-5-carboxyvaleryl, W is acetonyl, R² is {1-[2-(N,N-dimethylamino)ethyl]-1H-tetrazol-5-yl} thio and the nucleophilic compound is 5-mercapto-1-[2-(N,N-dimethylamino)ethyl]-1H-tetrazole.

28. A process as claimed in claim 9, wherein R¹ is 2-(2-imino-4-thiazolin-4-yl)acetyl, W is acetonyl, R² is {1-[2-(N,N-dimethylamino)ethyl]-1H-tetrazol-5-yl} thio and the nucleophilic compound is 5-mercapto-1-[2-(N,N-dimethylamino)ethyl]-1H-tetrazole.

29. A process as claimed in claim 9, wherein R¹ is D-5-phthalimido-5-carboxyvaleryl, W is acetonyl, R² is (1-methyl-1H-tetrazol-5-yl)thio, and the nucleophilic compound is 5-mercapto-1-methyl-1H-tetrazole.

* * * * *